United States Patent

Ohnishi et al.

Patent Number: 5,712,399
Date of Patent: Jan. 27, 1998

[54] N-SUBSTITUTED PHENYLCARBAMIC ACID DERIVATIVES, A PROCESS FOR PRODUCTION THEREOF, AGRICULTURAL AND HORTICULTURAL FUNGICIDES, INTERMEDIATES OF THE DERIVATIVES AND A PROCESS FOR PRODUCTION THEREOF

[75] Inventors: Masanobu Ohnishi, Oak Park, Ill.; Sohkichi Tajima, Osaka, Japan; Tsutomu Nishiguchi, Kawachinagano, Japan; Kenji Tsubata, Ibaraki, Japan

[73] Assignee: Nihon Nohyaku Co., Ltd., Tokyo, Japan

[21] Appl. No.: 816,969

[22] Filed: Mar. 13, 1997

Related U.S. Application Data

[62] Division of Ser. No. 529,048, Sep. 15, 1995, Pat. No. 5,650,434.

[30] Foreign Application Priority Data

Oct. 1, 1994 [JP] Japan .................. 6-261083

[51] Int. Cl.$^6$ .................................................. C07D 273/01
[52] U.S. Cl. ............................................................. 548/124
[58] Field of Search ............................................. 548/124

[56] References Cited

FOREIGN PATENT DOCUMENTS

| | | |
|---|---|---|
| 0498396 | 8/1992 | European Pat. Off. . |
| 0619301 | 10/1994 | European Pat. Off. . |
| 53-127478 | 11/1978 | Japan .................. 548/124 |
| WO 93/15046 | 8/1993 | WIPO . |

*Primary Examiner*—Robert Gerstl
*Attorney, Agent, or Firm*—Browdy and Neimark

[57] ABSTRACT

An N-substituted phenylcarbamic acid derivative represented by the general formula (I):

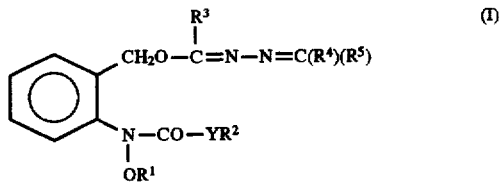

[wherein $R^1$ is H, a $(C_{1-6})$alkyl group, a halo$(C_{1-6})$alkyl group, a $(C_{1-6})$alkoxy$(C_{1-6})$alkyl group, a $(C_{2-6})$alkenyl group, a $(C_{2-6})$alkynyl group or a halo$(C_{1-6})$alkoxy$(C_{1-6})$alkyl group, $R^2$ is H, a $(C_{1-6})$alkyl group, a halo$(C_{1-6})$alkyl group, a $(C_{1-6})$alkoxy$(C_{1-6})$alkyl group, a $(C_{2-6})$alkenyl group, a $(C_{2-6})$alkynyl group, a halo$(C_{1-6})$alkoxy$(C_{1-6})$alkyl group or a cyano$(C_{1-6})$alkyl group, $R^3$ is a $(C_{1-6})$alkyl group or a halo$(C_{1-6})$alkyl group, each of $R^4$ and $R^5$ is a specific group, and Y is O or S] which is very effective in controlling powdery mildew, scab, late blight and gray mold; a process for producing said derivative; an agricultural and horticultural fungicide containing said derivative as an active ingredient; an intermediate of said derivative; and a process for producing the intermediate.

3 Claims, No Drawings

N-SUBSTITUTED PHENYLCARBAMIC ACID DERIVATIVES, A PROCESS FOR PRODUCTION THEREOF, AGRICULTURAL AND HORTICULTURAL FUNGICIDES, INTERMEDIATES OF THE DERIVATIVES AND A PROCESS FOR PRODUCTION THEREOF

This is a division of parent application Ser. No. 08/529,048 filed Sep. 15, 1995, now U.S. Pat. No. 5,650,434.

BACKGROUND OF THE INVENTION

1. Field of the Invention

The present invention relates to N-substituted phenylcarbamic acid derivatives represented by the following general formula (I), a process for production thereof, agricultural and horticultural fungicides, intermediate of the derivatives, and a process for production of the intermediates:

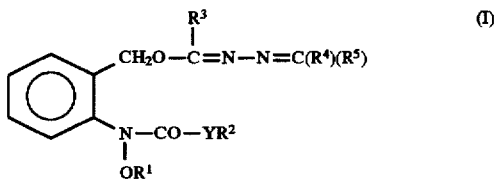

wherein $R^1$ is a hydrogen atom, a $(C_{1-6})$alkyl group, a halo$(C_{1-6})$alkyl group, a $(C_{1-6})$alkoxy$(C_{1-6})$alkyl group, a $(C_{2-6})$alkenyl group, a $(C_{2-6})$alkynyl group or a halo$(C_{1-6})$alkoxy$(C_{1-6})$alkyl group, $R^2$ is a hydrogen atom, a $(C_{1-6})$alkyl group, a halo$(C_{1-6})$alkyl group, a $(C_{1-6})$alkoxy$(C_{1-6})$alkyl group, a $(C_{2-6})$alkenyl group, a $(C_{2-6})$alkynyl group, a halo$(C_{1-6})$alkoxy$(C_{1-6})$alkyl group or a cyano$(C_{1-6})$alkyl group, $R^3$ is a $(C_{1-6})$alkyl group or a halo$(C_{1-6})$alkyl group, $R^4$ and $R^5$, which may be the same or different, are hydrogen atoms; cyano groups; $(C_{1-6})$alkyl groups; halo$(C_{1-6})$alkyl groups; $(C_{3-6})$cycloalkyl groups; halo$(C_{3-6})$cycloalkyl groups; $(C_{3-6})$cycloalkyl$(C_{1-6})$alkyl groups; $(C_{1-6})$alkoxy groups; halo$(C_{1-6})$alkoxy groups; $(C_{1-6})$alkylthio groups; halo$(C_{1-6})$alkylthio groups; $(C_{1-6})$alkoxy$(C_{1-6})$alkyl groups; $(C_{1-6})$alkylthio$(C_{1-6})$alkyl groups; $(C_{2-6})$alkenyl groups; halo$(C_{2-6})$alkenyl groups; $(C_{3-6})$cycloalkenyl groups; $(C_{2-6})$alkynyl groups; halo$(C_{2-6})$alkynyl groups; $(C_{1-6})$alkylcarbonyl groups; $(C_{1-6})$alkoxycarbonyl groups; unsubstituted phenyl groups; substituted phenyl groups having 1 to 5 substituents which may be the same or different and are selected from the group consisting of halogen atoms, cyano group, nitro group, formyl group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{2-6})$alkenyloxy groups, halo$(C_{2-6})$alkenyloxy groups, $(C_{2-6})$alkynyloxy groups, halo$(C_{2-6})$alkynyloxy groups, $(C_{2-6})$alkylcarbonyl groups, $(C_{1-6})$alkoxycarbonyl groups, di$(C_{1-6})$ alkylamino groups, di$(C_{2-6})$alkenylamino groups, di$(C_{2-6})$alkynylamino groups, unsubstituted phenyl$(C_{1-6})$ alkyl groups, substituted phenyl$(C_{1-6})$alkyl groups having 1 to 5 substituents which may be the same or different and are selected from the group consisting of $(C_{1-6})$alkyl groups, $(C_{1-6})$alkoxy groups and cyano group, unsubstituted phenoxy group, substituted phenoxy groups having 1 to 5 substituents which may be the same or different and are selected from the group consisting of $(C_{1-6})$alkyl groups, $(C_{1-6})$alkoxy groups and cyano group, unsubstituted heteroaryloxy groups, substituted heteroaryloxy groups having 1 to 5 substituents which may be the same or different and are selected from the group consisting of $(C_{1-6})$alkyl groups, $(C_{1-6})$alkoxy groups and cyano group, unsubstituted benzyloxy group, substituted benzyloxy groups having on the ring 1 to 5 substituents which may be the same or different and are selected from the group consisting of $(C_{1-6})$alkyl groups, $(C_{1-6})$alkoxy groups and cyano group, $(C_{1-6})$alkoxyimino$(C_{1-6})$alkyl groups, $(C_{1-3})$alkylenedioxy groups, and $(C_{2-6})$alkylene groups; unsubstituted phenoxy groups; substituted phenoxy groups having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkoxyimino$(C_{1-6})$alkyl groups and $(C_{1-3})$alkylenedioxy groups; unsubstituted phenylthio groups; substituted phenylthio groups having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$ alkoxy groups, halo$(C_{1-6})$alkoxy groups, $(C_{1-6})$ alkylthio groups, halo$(C_{1-6})$alkylthio groups, $(C_{1-6})$ alkoxyimino$(C_{1-6})$ alkyl groups and $(C_{1-3})$alkylenedioxy groups; unsubstituted phenyl$(C_{1-6})$alkyl groups; substituted phenyl$(C_{1-6})$alkyl groups having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$ alkoxy groups, halo$(C_{1-6})$alkoxy groups, $(C_{1-6})$ alkylthio groups, halo$(C_{1-6})$alkylthio groups, $(C_{1-6})$ alkoxyimino$(C_{1-6})$ alkyl groups and $(C_{3-6})$alkylenedioxy groups; unsubstituted phenyl$(C_{2-6})$alkenyl groups; substituted phenyl$(C_{2-6})$alkenyl groups having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$ alkylthio groups, halo$(C_{1-6})$alkylthio groups, $(C_{1-6})$ alkoxyimino$(C_{1-6})$alkyl groups and $(C_{3-6})$alkylenedioxy groups; unsubstituted phenylcarbonyl groups; substituted phenylcarbonyl groups having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkoxyimino$(C_{1-6})$alkyl groups and $(C_{1-3})$alkylenedioxy groups; unsubstituted phenoxycarbonyl groups; substituted phenoxycarbonyl groups having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$ alkoxy groups, $(C_{1-6})$alkylthio groups, halo$(C_{1-6})$alkylthio groups, $(C_{1-6})$alkoxyimino$(C_{1-6})$alkyl groups and $(C_{1-3})$ alkylenedioxy groups; unsubstituted phenoxy$(C_{1-6})$alkyl groups; substituted phenoxy$(C_{1-6})$alkyl groups having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$ alkoxy groups, $(C_{1-6})$alkylthio groups, halo$(C_{1-6})$alkylthio groups, $(C_{1-6})$alkoxyimino$(C_{1-6})$alkyl groups and $(C_{1-3})$ alkylenedioxy groups; unsubstituted phenylthio$(C_{1-6})$alkyl groups; substituted phenylthio$(C_{1-6})$alkyl groups having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$ alkoxy groups, $(C_{1-6})$alkylthio groups, halo$(C_{1-6})$alkylthio groups, $(C_{1-6})$alkoxyimino$(C_{1-6})$alkyl groups and $(C_{1-3})$ alkylenedioxy groups; unsubstituted phenyl($C_{1-6}$)alkylthio groups; substituted phenyl($C_{1-6}$)alkylthio groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$)alkoxy groups, halo($C_{1-6}$) alkoxy groups, ($C_{1-6}$)alkylthio groups, halo($C_{1-6}$)alkylthio groups, ($C_{1-6}$)alkoxyimino($C_{1-6}$)alkyl groups and ($C_{3-6}$) alkylenedioxy groups; unsubstituted phenyl($C_{1-6}$) alkylcarbonyl groups; substituted phenyl($C_{1-6}$) alkylcarbonyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$)alkylthio groups, halo($C_{1-6}$)alkylthio groups, ($C_{1-6}$)alkoxyimino($C_{1-6}$) alkyl groups and ($C_{1-3}$)alkylenedioxy groups; unsubstituted phenyl($C_{1-6}$)alkoxycarbonyl groups; substituted phenyl ($C_{1-6}$) alkoxycarbonyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$)alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$)alkylenedioxy groups; 5- to 7-membered heterocyclic rings having 1 to 3 heteroatoms which may be the same or different and are selected from the group consisting of oxygen atom, sulfur atom and nitrogen atom; heterocyclic rings having a benzene ring condensed therewith; or heterocyclic rings having a ($C_{3-6}$)cycloalkane group condensed therewith; the above heterocyclic rings being able to have one or more substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxycarbonyl groups, unsubstituted phenyl group, substituted phenyl groups having 1 to 5 substituents which may be the same or different and are selected from the group consisting of halogen atoms and ($C_{1-6}$)alkyl groups, phenyl ($C_{1-6}$)alkyl groups, pyridyl group, pyrimidyl group and dioxolane group, and Y is an oxygen atom or a sulfur atom.

2. Related Art

EP Laid-Open No. 0498396 and WO93/15046 disclose that N-phenylcarbamate derivatives are useful as agricultural and horticultural fungicides.

SUMMARY OF THE INVENTION

The present inventors earnestly investigated for developing a novel agricultural and horticultural fungicide and consequently found that the N-substituted phenylcarbamic acid derivatives of the present invention are novel compounds not known in any literature and are useful as agricultural and horticultural fungicides, whereby the present invention has been accomplished.

DETAILED DESCRIPTION OF THE PREFERRED EMBODIMENTS

In the definition of the substituents of the N-substituted phenylcarbamic acid derivative of the general formula (I) of the present invention, the prefix "halo" is used for expressing that a group contains one or more halogen atoms selected from chlorine, fluorine, bromine and iodine atoms. For example, the term "haloalkyl group" means a substituted alkyl group having as the substituent(s) one or more halogen atoms which may be the same or different and are selected from the group consisting of chlorine atom, fluorine atom, bromine atom and iodine atom. The prefix "($C_{1-6}$)" indicates the number of carbon atoms of each substituent.

Preferable examples of substituent for $R^1$ are linear or branched ($C_{1-6}$)alkyl groups such as methyl, ethyl, n-propyl, i-propyl, n-butyl, i-butyl, s-butyl, t-butyl, n-pentyl, n-hexyl, etc. Of these, methyl group and ethyl group are particularly preferable.

Preferable examples of substituent for $R^2$ are linear or branched ($C_{1-6}$)alkyl groups such as methyl, ethyl, n-propyl, i-propyl, n-butyl, i-butyl, s-butyl, t-butyl, n-pentyl, n-hexyl, etc. Of these, methyl group is particulary preferable.

Preferable examples of substituent for $R^3$ are linear or branched ($C_{1-6}$)alkyl groups such as methyl, ethyl, n-propyl, i-propyl, n-butyl, i-butyl, s-butyl, t-butyl, n-pentyl, n-hexyl, etc. Of these, methyl group and ethyl group are particularly preferable.

Preferable examples of substituents for $R^4$ and $R^5$, respectively, which may be the same or different are linear or branched ($C_{1-6}$)alkyl groups such as methyl, ethyl, n-propyl, i-propyl, n-butyl, i-butyl, s-butyl, t-butyl, n-pentyl, n-hexyl, etc.; unsubstituted phenyl group; substituted phenyl groups having 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$)alkoxy groups, halo($C_{1-6}$) alkoxy groups, ($C_{1-6}$)alkylthio groups and halo($C_{1-6}$) alkylthio groups; 5- or 6-membered heterocyclic rings having 1 to 3 heteroatoms which may be the same or different and are selected from the group consisting of oxygen atom, sulfur atom and nitrogen atom; and said 5- or 6-membered heterocyclic rings which have 1 to 4 substituents selected from halogen atoms.

As substituent for Y, oxygen atom is preferable.

The N-substituted phenylcarbamic acid derivative of the general formula (I) of the present invention can be produced, for example, by the following process.

Production process 1.

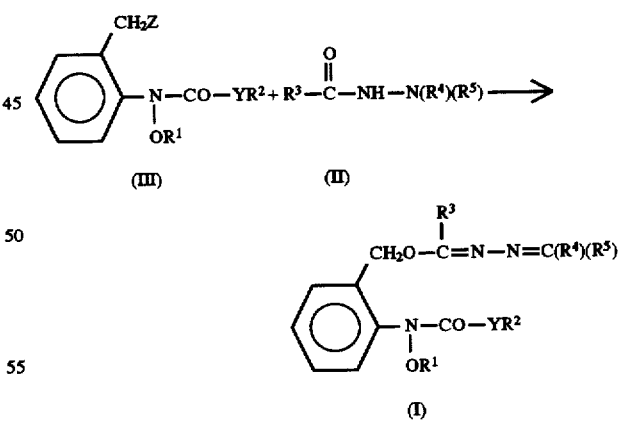

wherein $R^1$, $R^2$, $R^3$, $R^4$, $R^5$ and Y are as defined above and Z is a halogen atom.

The N-substituted phenylcarbamic acid derivative of the general formula (I) can be produced by reacting a compound of the general formula (III) with a compound of the general formula (II) in the presence of a base or a silver compound, and an inert solvent.

As the inert solvent usable in this reaction, any inert solvent may be used so long as it does not markedly inhibit the progress of the reaction. There may be used, for example, alcohols such as isopropanol, tert-butanol, diethylene glycol, etc.; ketones such as acetone, methyl ethyl ketone, cyclohexanone, etc.; ethers such as diethyl ether, diisopropyl ether, tetrahydrofuran, dioxane, monoglyme, diglyme, etc.; halogenated hydrocarbons such as dichloroethane, chloroform, carbon tetrachloride, tetrachloroethane, etc.; aromatic hydrocarbons such as benzene, chlorobenzene, nitrobenzene, toluene, etc.; nitriles such as acetonitrile, etc.; dimethylformamide; dimethyl sulfoxide; and water. These inert solvents may be used singly or as a mixture thereof.

Two-phase reaction can be carried out as the above reaction by using water and a water-insoluble inert solvent. In this case, there can be used phase transfer catalysts such as triethylbenzylammonium chloride, trioctylmethylammonium chloride, etc.

As the base used in the reaction, an inorganic base or an organic base may be used. As the inorganic base, there may be used, for example, carbonates or hydroxides of alkali metal atoms or alkaline earth metal atoms, such as sodium carbonate, potassium carbonate, calcium carbonate, sodium hydrogencarbonate, sodium hydroxide, potassium hydroxide, calcium hydroxide, etc., and hydrides of alkali metal atoms, such as lithium hydride, sodium hydride, etc. As the organic base, there may be used, for example, alkoxides of alkali metal atoms, such as sodium methoxide, potassium tertbutoxide, etc., diethylamine, triethylamine, pyridine, and benzyltrimethylammonium hydroxide. These bases may be used singly or as a mixture thereof. The amount of the base used may be properly chosen in the range of 1 mole to excess moles per mole of the compound of the general formula (III).

As the silver compound usable in the reaction, silver oxide, for example, may be used. The amount of the silver compound used may be properly chosen in the range of 1 mole to excess moles per mole of the compound of the general formula (III).

Since the reaction is an equimolar reaction, it is sufficient that the compound of the general formula (III) and the compound of the general formula (II) are used in equimolar amounts, though either of them may be used in excess.

The reaction temperature is properly chosen in the range of −70° C. to the boiling point of the inert solvent used. It is preferably −40° C. to room temperature.

Although the reaction time is varied depending on the reaction temperature, the scale of reaction, etc., it is usually chosen in the range of 30 minutes to 48 hours.

After completion of the reaction, the desired compound is isolated from the reaction mixture by a conventional method, and if necessary, purified by column chromatography, recrystallization, etc., whereby the N-substituted phenylcarbamic acid derivative of the general formula (I) can be produced.

The compound of the general formula (III), i.e., the starting compound for producing the N-substituted phenylcarbamic acid derivative of the general formula (I) of the present invention can be produced, for example, by the process illustrated below.

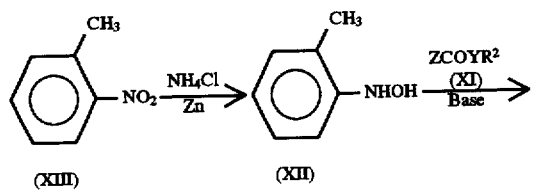

(XIII)  (XII)

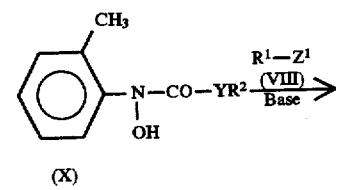

(X)

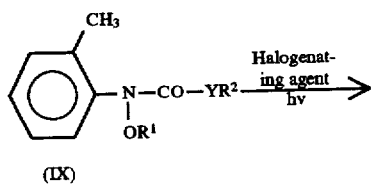

(IX)

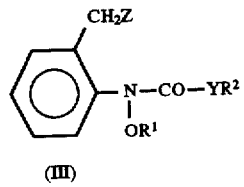

(III)

wherein $R^1$, $R^2$, Z and Y are as defined above, and $Z^1$ is a halogen atom or a group of $-OSO_2R^8$ wherein $R^8$ is a group of $-OR^1$ wherein $R^1$ is as defined above, $(C_{1-6})$alkyl groups, an unsubstituted phenyl group, or substituted phenyl groups having on the ring 1 to 5 substituents which may be the same or different and are selected from the groups consisting of halogen atoms, cyano group, nitro group, $(C_{1-6})$alkyl groups, and $(C_{1-6})$alkoxy groups.

o-Nitrotoluene of the structural formula (XIII) is reacted with ammonium chloride in the presence of zinc to prepare N-2-methylphenylhydroxyamine of the structural formula (XII) (Organic Syntheses Collective Volume III, p. 668, 1955). The hydroxyamine is reacted with a compound of the general formula (XI) in the presence of a base after or without isolation of the hydroxyamine to obtain a compound of the general formula (X). This compound (X) is reacted with a compound of the general formula (VIII) in the presence of a base after or without isolation of the compound (X) to obtain a compound of the general formula (IX). This compound (IX) is reacted with a halogenating agent under light irradiation after or without isolation of the compound (IX), whereby the compound of the general formula (III) can be produced.

Production process 2.

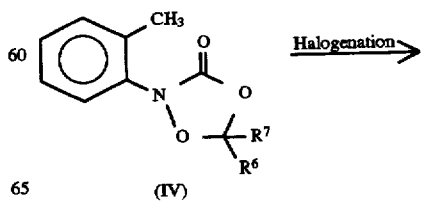

(IV)

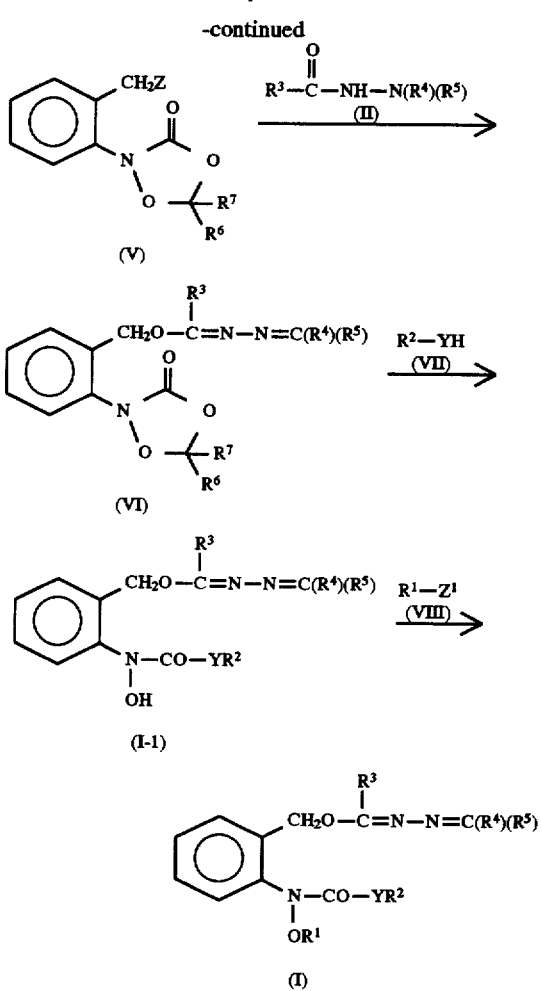

wherein, $R^1$, $R^2$, $R^3$, $R^4$, $R^5$, Y, Z and $Z^1$ are as defined above, and $R^6$ and $R^7$, which may be the same or different, are hydrogen atoms, ($C_{1-6}$)alkyl groups, ($C_{3-6}$)cycloakyl groups, unsubstituted phenyl groups, or substituted phenyl group having 1 to 5 substituents which may be the same or different and which are selected from the group consisting of halogen atoms, cyano group, nitro group and ($C_{1-6}$)alkyl groups, $R^6$ and $R^7$ being able to be taken together to represent a ($C_{2-6}$)alkylene group.

A compound of the general formula (IV) is reacted with a halogenating agent in the presence or absence of an inert solvent to obtain a compound of the general formula (V). The compound (V) is reacted with a compound of the general formula (II) in the presence of an inert solvent and a base or a silver salt after or without isolation of the compound (V) to obtain a compound of the general formula (VI). The compound (VI) is reacted with a compound of the general formula (VII) in the presence or absence of an inert solvent and in the presence of a base after or without isolation of the compound (VI) to obtain an N-substituted phenylcarbamic acid derivative of the general formula (I-1). The derivative (I-1) is reacted with a compound of the general formula (VIII) in the presence or absence of an inert solvent and in the presence of a base after or without isolation of the derivative (I-1), whereby an N-substituted phenylcarbamic acid derivative of the general formula (I) can be produced.

① General formula (IV)→general formula (V)

As the inert solvent usable in this reaction, there can be used, for example, halogenated hydrocarbons such as chloroform, carbon tetrachloride, etc.; aromatic hydrocarbons such as benzene, etc.; and halogenated aromatic hydrocarbons such as chlorobenzene, fluorobenzene, dichlorobenzene, etc. These inert solvents may be used singly or as a mixture thereof.

As the halogenating agent, there can be used halogenating agents such as chlorine, bromine, iodine, N-chlorosuccinimide, N-bromosuccinimide, etc. The amount of the halogenating agent used may be chosen in the range of 0.8 to 2.0 moles, preferably 0.9 to 1.2 moles, per mole of the compound of the general formula (IV).

For accelerating the progress of the reaction, a catalytic amount of an azo compound such as azobis(isobutylonitrile) or a peroxide such as benzoyl peroxide may be used, or the reaction may be carried out under light irradiation.

As to the reaction temperature, the reaction is carried out in the range of room temperature to the boiling point of the inert solvent used, preferably 70°–110° C.

Although the reaction time is varied depending on the reaction temperature, the scale of reaction, etc., it is chosen in the range of several minutes to 24 hours.

After completion of the reaction, the desired compound is isolated from the reaction mixture containing the desired compound by a conventional method, and if necessary, purified by column chromatography, etc., whereby the compound of the general formula (V) can be produced.

The desired compound obtained by the reaction may be subjected to the subsequent reaction without isolation.

Examples of the compound of the general formula (V) are given in Table 1 but they are not intended in any way to limit the scope of the present invention.

TABLE 1

General formula (V)

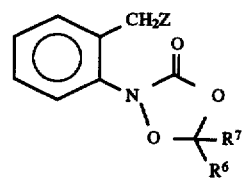

(V)

| No | Z | $R^6$ | $R^7$ | Physical property |
|---|---|---|---|---|
| V-1 | Cl | H | H | |
| V-2 | Br | H | H | Paste |
| V-3 | I | H | H | |
| V-4 | Cl | $CH_3$ | $CH_3$ | |
| V-5 | Br | $CH_3$ | $CH_3$ | |

The compound of the general formula (IV) can be produced, for example, by the production process disclosed in Japanese Patent Unexamined Publication No. 53-127478.

② General formula (V)→general formula (VI)

The compound of the general formula (VI) can be produced by carrying out this reaction according to production process 1.

Examples of the compound of the general formula (VI) are given in Table 2 but they are not intended in any way to limit the scope of the present invention.

TABLE 2

General formula (VI)
(wherein Ph is a phenyl group and $R^3$ is $CH_3$)

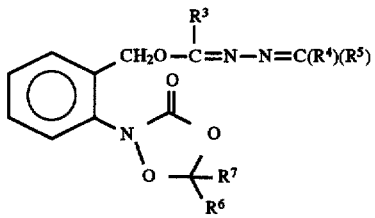

(VI)

| No | $R^4$ | $R^5$ | $R^6$ | $R^7$ | Physical property |
|---|---|---|---|---|---|
| VI-1 | CH$_3$ | Ph | H | H | |
| VI-2 | C$_2$H$_5$ | Ph | H | H | |
| VI-3 | CH$_3$ | Ph | CH$_3$ | CH$_3$ | |
| VI-4 | CH$_3$ | 2-F—Ph | H | H | |
| VI-5 | C$_2$H$_5$ | 2-F—Ph | H | H | |
| VI-6 | CH$_3$ | 2-F—Ph | CH$_3$ | CH$_3$ | |
| VI-7 | CH$_3$ | 3-F—Ph | H | H | $^1$H-NMR |
| VI-8 | C$_2$H$_5$ | 3-F—Ph | H | H | |
| VI-9 | CH$_3$ | 3-F—Ph | CH$_3$ | CH$_3$ | |
| VI-10 | CH$_3$ | 4-F—Ph | H | H | |
| VI-11 | C$_2$H$_5$ | 4-F—Ph | H | H | |
| VI-12 | CH$_3$ | 4-F—Ph | CH$_3$ | CH$_3$ | |
| VI-13 | CH$_3$ | 2-Cl—Ph | H | H | |
| VI-14 | C$_2$H$_5$ | 2-Cl—Ph | H | H | |
| VI-15 | CH$_3$ | 2-Cl—Ph | CH$_3$ | CH$_3$ | |
| VI-16 | CH$_3$ | 3-Cl—Ph | H | H | |
| VI-17 | C$_2$H$_5$ | 3-Cl—Ph | H | H | |
| VI-18 | CH$_3$ | 3-Cl—Ph | CH$_3$ | CH$_3$ | |
| VI-19 | CH$_3$ | 4-Cl—Ph | H | H | $^1$H-NMR |
| VI-20 | C$_2$H$_5$ | 4-Cl—Ph | H | H | |
| VI-21 | CH$_3$ | 4-Cl—Ph | CH$_3$ | CH$_3$ | |
| VI-22 | CH$_3$ | 2-Br—Ph | H | H | |
| VI-23 | C$_2$H$_5$ | 2-Br—Ph | H | H | |
| VI-24 | CH$_3$ | 2-Br—Ph | CH$_3$ | CH$_3$ | |
| VI-25 | CH$_3$ | 3-Br—Ph | H | H | |
| VI-26 | C$_2$H$_5$ | 3-Br—Ph | H | H | |
| VI-27 | CH$_3$ | 3-Br—Ph | CH$_3$ | CH$_3$ | |
| VI-28 | CH$_3$ | 4-Br—Ph | H | H | |
| VI-29 | C$_2$H$_5$ | 4-Br—Ph | H | H | |
| VI-30 | CH$_3$ | 4-Br—Ph | CH$_3$ | CH$_3$ | |
| VI-31 | CH$_3$ | 2-CH$_3$—Ph | H | H | |
| VI-32 | C$_2$H$_5$ | 2-CH$_3$—Ph | H | H | |
| VI-33 | CH$_3$ | 2-CH$_3$—Ph | CH$_3$ | CH$_3$ | |
| VI-34 | CH$_3$ | 3-CH$_3$—Ph | H | H | |
| VI-35 | C$_2$H$_5$ | 3-CH$_3$—Ph | H | H | |
| VI-36 | CH$_3$ | 3-CH$_3$—Ph | CH$_3$ | CH$_3$ | |
| VI-37 | CH$_3$ | 4-CH$_3$—Ph | H | H | |
| VI-38 | C$_2$H$_5$ | 4-CH$_3$—Ph | H | H | |
| VI-39 | CH$_3$ | 4-CH$_3$—Ph | CH$_3$ | CH$_3$ | |
| VI-40 | CH$_3$ | 2-CH$_3$O—Ph | H | H | |
| VI-41 | C$_2$H$_5$ | 2-CH$_3$O—Ph | H | H | |
| VI-42 | CH$_3$ | 2-CH$_3$O—Ph | CH$_3$ | CH$_3$ | |
| VI-43 | CH$_3$ | 3-CH$_3$O—Ph | H | H | |
| VI-44 | C$_2$H$_5$ | 3-CH$_3$O—Ph | H | H | |
| VI-45 | CH$_3$ | 3-CH$_3$O—Ph | CH$_3$ | CH$_3$ | |
| VI-46 | CH$_3$ | 4-CH$_3$O—Ph | H | H | |
| VI-47 | C$_2$H$_5$ | 4-CH$_3$O—Ph | H | H | |
| VI-48 | CH$_3$ | 4-CH$_3$O—Ph | CH$_3$ | CH$_3$ | |
| VI-49 | CH$_3$ | 2-CN—Ph | H | H | |
| VI-50 | C$_2$H$_5$ | 2-CN—Ph | H | H | |
| VI-51 | CH$_3$ | 2-CN—Ph | CH$_3$ | CH$_3$ | |
| VI-52 | CH$_3$ | 3-CN—Ph | H | H | |
| VI-53 | C$_2$H$_5$ | 3-CN—Ph | H | H | |
| VI-54 | CH$_3$ | 3-CN—Ph | CH$_3$ | CH$_3$ | |
| VI-55 | CH$_3$ | 4-CN—Ph | H | H | |
| VI-56 | C$_2$H$_5$ | 4-CN—Ph | H | H | |
| VI-57 | CH$_3$ | 4-CN—Ph | CH$_3$ | CH$_3$ | |
| VI-58 | CH$_3$ | 2-NO$_2$—Ph | H | H | |
| VI-59 | C$_2$H$_5$ | 2-NO$_2$—Ph | H | H | |
| VI-60 | CH$_3$ | 2-NO$_2$—Ph | CH$_3$ | CH$_3$ | |
| VI-61 | CH$_3$ | 3-NO$_2$—Ph | H | H | $^1$H-NMR |

TABLE 2-continued

General formula (VI)
(wherein Ph is a phenyl group and $R^3$ is $CH_3$)

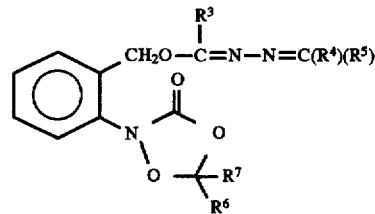

(VI)

| No | $R^4$ | $R^5$ | $R^6$ | $R^7$ | Physical property |
|---|---|---|---|---|---|
| VI-62 | C$_2$H$_5$ | 3-NO$_2$—Ph | H | H | |
| VI-63 | CH$_3$ | 3-NO$_2$—Ph | CH$_3$ | CH$_3$ | |
| VI-64 | CH$_3$ | 4-NO$_2$—Ph | H | H | |
| VI-65 | C$_2$H$_5$ | 4-NO$_2$—Ph | H | H | |
| VI-66 | CH$_3$ | 4-NO$_2$—Ph | CH$_3$ | CH$_3$ | |
| VI-67 | CH$_3$ | 2,4-F$_2$—Ph | H | H | |
| VI-68 | C$_2$H$_5$ | 2,4-F$_2$—Ph | H | H | |
| VI-69 | CH$_3$ | 2,4-F$_2$—Ph | CH$_3$ | CH$_3$ | |
| VI-70 | CH$_3$ | 3,4-F$_2$—Ph | H | H | $^1$H-NMR |
| VI-71 | C$_2$H$_5$ | 3,4-F$_2$—Ph | H | H | |
| VI-72 | CH$_3$ | 3,4-F$_2$—Ph | CH$_3$ | CH$_3$ | |
| VI-73 | CH$_3$ | 2,4-Cl$_2$—Ph | H | H | $^1$H-NMR |
| VI-74 | C$_2$H$_5$ | 2,4-Cl$_2$—Ph | H | H | |
| VI-75 | CH$_3$ | 2,4-Cl$_2$—Ph | CH$_3$ | CH$_3$ | |
| VI-76 | CH$_3$ | 3,4-Cl$_2$—Ph | H | H | |
| VI-77 | C$_2$H$_5$ | 3,4-Cl$_2$—Ph | H | H | |
| VI-78 | CH$_3$ | 3,4-Cl$_2$—Ph | CH$_3$ | CH$_3$ | |
| VI-79 | CH$_3$ | 2,5-(CH$_3$)$_2$—Ph | H | H | |
| VI-80 | C$_2$H$_5$ | 2,5-(CH$_3$)$_2$—Ph | H | H | |
| VI-81 | CH$_3$ | 2,5-(CH$_3$)$_2$—Ph | CH$_3$ | CH$_3$ | |
| VI-82 | CH$_3$ | 3,4-(CH$_3$)$_2$—Ph | H | H | |
| VI-83 | C$_2$H$_5$ | 3,4-(CH$_3$)$_2$—Ph | H | H | |
| VI-84 | CH$_3$ | 3,4-(CH$_3$)$_2$—Ph | CH$_3$ | CH$_3$ | |
| VI-85 | CH$_3$ | 3,4-(CH$_3$O)$_2$—Ph | H | H | |
| VI-86 | C$_2$H$_5$ | 3,4-(CH$_3$O)$_2$—Ph | H | H | |
| VI-87 | CH$_3$ | 3,4-(CH$_3$O)$_2$—Ph | CH$_3$ | CH$_3$ | |
| VI-88 | CH$_3$ | Pyridin-2-yl | H | H | |
| VI-89 | C$_2$H$_5$ | Pyridin-2-yl | H | H | |
| VI-90 | CH$_3$ | Pyridin-2-yl | CH$_3$ | CH$_3$ | |
| VI-91 | CH$_3$ | Pyridin-3-yl | H | H | |
| VI-92 | C$_2$H$_5$ | Pyridin-3-yl | H | H | |
| VI-93 | CH$_3$ | Pyridin-3-yl | CH$_3$ | CH$_3$ | |
| VI-94 | CH$_3$ | Pyridin-4-yl | H | H | |
| VI-95 | C$_2$H$_5$ | Pyridin-4-yl | H | H | |
| VI-96 | CH$_3$ | Pyridin-4-yl | CH$_3$ | CH$_3$ | |
| VI-97 | CH$_3$ | Tetralin-4-yl | H | H | |
| VI-98 | C$_2$H$_5$ | Tetralin-4-yl | H | H | |
| VI-99 | CH$_3$ | Tetralin-4-yl | CH$_3$ | CH$_3$ | |
| VI-100 | CH$_3$ | Indan-5-yl | H | H | |
| VI-101 | C$_2$H$_5$ | Indan-5-yl | H | H | |
| VI-102 | CH$_3$ | Indan-5-yl | CH$_3$ | CH$_3$ | |

Table 2-1 shows $^1$H-NMR data of compounds having a physical property expressed by the word "$^1$H-NMR" in Table 2.

TABLE 2-1

| No | $^1$H-NMR data [300 MHz, CDCl$_3$/TMS, δ value (ppm)] |
|---|---|
| VI-7 | 2.39 (s, 3H), 2.298 (s, 3H), 5.431 (s, 2H), 5.716 (s, 2H), 7.03–7.12 (m, 1H), 7.3–7.65 (m, 7H) |
| VI-19 | 2.23 (s, 3H), 2.29 (s, 3H), 5.42 (s, 2H), 5.72 (s, 2H), 7.35 (d, 2H), 7.40–7.49 (m, 3H), 7.50–7.56 (m, 1H), 7.57–7.61 (m, 1H), 7.78 (d, 2H). |
| VI-61 | 2.264 (s, 3H), 2.357 (s, 3H), 5.437 (s, 2H), 5.732 (s, 2H), 7.4–7.65 (m, 5H), 8.15–8.25 (m, 2H), 8.5–8.9 (m, 1H). |
| VI-70 | 2.232 (s, 3H), 2.274 (s, 3H), 5.416 (s, 2H), |

TABLE 2-1-continued

| No | $^1$H-NMR data [300 MHz, CDCl$_3$/TMS, δ value (ppm)] |
|---|---|
| VI-73 | 5.723 (s, 2H), 7.1–7.2 (dd, 1H), 7.4–7.63 (m, 5H), 7.67–7.77 (m, 1H). 2.159 (s, 3H), 2.236 (s, 3H), 5.411 (s, 2H), 5.723 (s, 2H), 7.24–7.65 (m, 7H). |

③ General formula (VI)→general formula (I-1)

As the inert solvent and the base which are usable in this reaction, there can be used, for example, the inert solvents and the bases, respectively, exemplified in production process 1. The compound of the general formula (VII) may be used in excess to serve also as the inert solvent.

The amount of the base used may be properly chosen in the range of 1 mole to excess moles per mole of the compound of the general formula (VI).

Since the reaction is an equimolar reaction, it is sufficient that the compound of the general formula (VI) and the compound of the general formula (VII) are used in equimolar amounts, though either of them may be used in excess.

The reaction temperature is preferably in the range of 0° C. to the boiling point of the inert solvent used, and is more preferably a temperature near room temperature.

Although the reaction time is varied depending on the reaction temperature, the scale of reaction, etc., it is chosen in the range of several minutes to 24 hours.

After completion of the reaction, the desired compound is isolated from the reaction mixture containing the desired compound by a conventional method, and if necessary, purified by column chromatography, etc., whereby the N-substituted carbamic acid derivative of the general formula (I-1) can be produced.

The desired compound obtained by the reaction may be subjected to the subsequent reaction without isolation.

④ General formula (I-1)→general formula (I)

The N-substituted carbamic acid derivative of the general formula (I) can be produced by carrying out this reaction in a manner similar to the synthesys of the general formula (IX) described in the production process 1. The reaction temperature is preferably in the boiling range of the inert solvent used.

Typical compounds as the N-substituted carbamic acid derivatives of the general formula (I) produced by production processes 1 and 2 are listed in Table 3 but they are not intended in any way to limit the scope of the present invention.

TABLE 3

(wherein Ph = a phenyl group; R$^3$ = CH$_3$ and Y = O in the general formula (1))

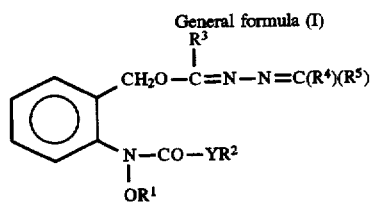

General formula (I)

| No | R$^1$ | R$^2$ | R$^4$ | R$^5$ | Physical property |
|---|---|---|---|---|---|
| 1 | H | CH$_3$ | CH$_3$ | Ph | $^1$H—NMR |
| 2 | H | CH$_3$ | CH$_3$ | 3-F—Ph | $^1$H—NMR |
| 3 | H | CH$_3$ | CH$_3$ | 4-Cl—Ph | $^1$H—NMR |
| 4 | H | CH$_3$ | CH$_3$ | 3-NO$_2$—Ph | $^1$H—NMR |
| 5 | H | CH$_3$ | CH$_3$ | 3,4-F$_2$—Ph | $^1$H—NMR |
| 6 | H | CH$_3$ | CH$_3$ | 2,4-Cl$_2$—Ph | $^1$H—NMR |
| 7 | H | CH$_3$ | CH$_3$ | 3,4-(CH$_3$)—Ph | $^1$H—NMR |
| 8 | CH$_3$ | CH$_3$ | CH$_3$ | Ph | nD 1.5765 (19.5° C.) |
| 9 | CH$_3$ | CH$_3$ | CH$_3$ | 2-F—Ph | |
| 10 | CH$_3$ | CH$_3$ | CH$_3$ | 3-F—Ph | nD 1.5654 (19.0° C.) |
| 11 | CH$_3$ | CH$_3$ | CH$_3$ | 4-F—Ph | nD 1.5645 (22.6° C.) |
| 12 | CH$_3$ | CH$_3$ | CH$_3$ | 2,4-F$_2$—Ph | nD 1.5534 (19.4° C.) |
| 13 | CH$_3$ | CH$_3$ | CH$_3$ | 2,5-F$_2$—Ph | |
| 14 | CH$_3$ | CH$_3$ | CH$_3$ | 4-F-3-NO$_2$—Ph | nD 1.5682 (19.6° C.) |
| 15 | CH$_3$ | CH$_3$ | CH$_3$ | 3,4-F$_2$—Ph | nD 1.5613 (18.7° C.) |
| 16 | CH$_3$ | CH$_3$ | CH$_3$ | 2,6-F$_2$—Ph | nD 1.5479 (22.5° C.) |
| 17 | CH$_3$ | CH$_3$ | CH$_3$ | 2,4,5-F$_3$—Ph | nD 1.5449 (23.9° C.) |
| 18 | CH$_3$ | CH$_3$ | CH$_3$ | 2,4,6-F$_3$—Ph | |
| 19 | CH$_3$ | CH$_3$ | CH$_3$ | 2,3,4,5,6-F$_5$—Ph | |
| 20 | CH$_3$ | CH$_3$ | CH$_3$ | 2-Cl—Ph | |
| 21 | CH$_3$ | CH$_3$ | CH$_3$ | 3-Cl—Ph | nD 1.5814 (21.3° C.) |
| 22 | CH$_3$ | CH$_3$ | CH$_3$ | 4-Cl—Ph | m.p. 64.2–65.2° C. |
| 23 | CH$_3$ | CH$_3$ | CH$_3$ | 2,3-Cl$_2$—Ph | |
| 24 | CH$_3$ | CH$_3$ | CH$_3$ | 2,4-Cl$_2$—Ph | |
| 25 | CH$_3$ | CH$_3$ | CH$_3$ | 2,5-Cl$_2$—Ph | |
| 26 | CH$_3$ | CH$_3$ | CH$_3$ | 2,6-Cl$_2$—Ph | |
| 27 | CH$_3$ | CH$_3$ | CH$_3$ | 3,4-Cl$_2$—Ph | nD 1.5874 (21.7° C.) |
| 28 | CH$_3$ | CH$_3$ | CH$_3$ | 3,5-Cl$_2$—Ph | |
| 29 | CH$_3$ | CH$_3$ | CH$_3$ | 2,4,5-Cl$_3$—Ph | |
| 30 | CH$_3$ | CH$_3$ | CH$_3$ | 3,4,5-Cl$_3$—Ph | |
| 31 | CH$_3$ | CH$_3$ | CH$_3$ | 2-Br-Ph | |
| 32 | CH$_3$ | CH$_3$ | CH$_3$ | 3-Br-Ph | nD 1.5752 (26.9° C.) |
| 33 | CH$_3$ | CH$_3$ | CH$_3$ | 4-Br-Ph | nD 1.6025 (7.8° C.) |
| 34 | CH$_3$ | CH$_3$ | CH$_3$ | 2-I—Ph | |
| 35 | CH$_3$ | CH$_3$ | CH$_3$ | 3-I—Ph | nD 1.6092 (10.4° C.) |
| 36 | CH$_3$ | CH$_3$ | CH$_3$ | 4-I—Ph | |
| 37 | CH$_3$ | CH$_3$ | CH$_3$ | 3-Br-4-F—Ph | nD 1.5739 (12.6° C.) |
| 38 | CH$_3$ | CH$_3$ | CH$_3$ | 2-CH$_3$—Ph | nD 1.5641 (18.3° C.) |
| 39 | CH$_3$ | CH$_3$ | CH$_3$ | 3-CH$_3$—Ph | nD 1.5358 (19.4° C.) |
| 40 | CH$_3$ | CH$_3$ | CH$_3$ | 4-CH$_3$—Ph | nD 1.5695 (19.1° C.) |
| 41 | CH$_3$ | CH$_3$ | CH$_3$ | 4-Cl-3-CH$_3$—Ph | nD 1.5828 (12.6° C.) |
| 42 | CH$_3$ | CH$_3$ | CH$_3$ | 3,4-(CH$_3$)$_2$—Ph | nD 1.5735 (19.6° C.) |
| 43 | CH$_3$ | CH$_3$ | CH$_3$ | 2,5-(CH$_3$)$_2$—Ph | nD 1.5614 (22.4° C.) |
| 44 | CH$_3$ | CH$_3$ | CH$_3$ | 3-CH$_3$—4-F—Ph | nD 1.5690 (22.8° C.) |
| 45 | CH$_3$ | CH$_3$ | CH$_3$ | 2-F-4-Cl-5-CH$_3$—Ph | nD 1.5704 (22.7° C.) |

TABLE 3-continued (wherein Ph = a phenyl group; $R^3$ = $CH_3$ and Y = O in the general formula (1))

General formula (I)

$$\underset{\underset{OR^1}{|}}{\underset{N-CO-YR^2}{\overset{CH_2O-\overset{R^3}{\underset{|}{C}}=N-N=C(R^4)(R^5)}{\bigcirc}}} \quad (I)$$

| No | $R^1$ | $R^2$ | $R^4$ | $R^5$ | Physical property |
|----|-------|-------|-------|-------|-------------------|
| 46 | $CH_3$ | $CH_3$ | $CH_3$ | 2-$CH_3O$—Ph | nD 1.5529 (23.0° C.) |
| 47 | $CH_3$ | $CH_3$ | $CH_3$ | 3-$CH_3O$—Ph | |
| 48 | $CH_3$ | $CH_3$ | $CH_3$ | 4-$CH_3O$—Ph | |
| 49 | $CH_3$ | $CH_3$ | $CH_3$ | 3-i-$C_4H_9O$—Ph | nD 1.5610 (18.7° C.) |
| 50 | $CH_3$ | $CH_3$ | $CH_3$ | 3-s-$C_4H_9O$—Ph | nD 1.5589 (19.0° C.) |
| 51 | $CH_3$ | $CH_3$ | $CH_3$ | 3,4-$(CH_3O)_2$—Ph | m.p. 104.5–105.8° C. |
| 52 | $CH_3$ | $CH_3$ | $CH_3$ | 2-$C_2H_5$—Ph | |
| 53 | $CH_3$ | $CH_3$ | $CH_3$ | 3-$C_2H_5$—Ph | |
| 54 | $CH_3$ | $CH_3$ | $CH_3$ | 4-$C_2H_5$—Ph | nD 1.5725 (17.2° C.) |
| 55 | $CH_3$ | $CH_3$ | $CH_3$ | 4-i-$C_3H_7$—Ph | m.p. 83.9–87.0° C. |
| 56 | $CH_3$ | $CH_3$ | $CH_3$ | 4-i-$C_4H_9$—Ph | m.p. 53.5–55.5° C. |
| 57 | $CH_3$ | $CH_3$ | $CH_3$ | 2-$CF_3$—Ph | |
| 58 | $CH_3$ | $CH_3$ | $CH_3$ | 3-$CF_3$—Ph | nD 1.5420 (22.9° C.) |
| 59 | $CH_3$ | $CH_3$ | $CH_3$ | 4-$CF_3$—Ph | |
| 60 | $CH_3$ | $CH_3$ | $CH_3$ | 2-$CF_3O$—Ph | |
| 61 | $CH_3$ | $CH_3$ | $CH_3$ | 3-$CF_3O$—Ph | nD 1.5354 (23.9° C.) |
| 62 | $CH_3$ | $CH_3$ | $CH_3$ | 4-$CF_3O$—Ph | nD 1.5376 (16.8° C.) |
| 63 | $CH_3$ | $CH_3$ | $CH_3$ | 2-$CHF_2O$—Ph | |
| 64 | $CH_3$ | $CH_3$ | $CH_3$ | 3-$CHF_2O$—Ph | nD 1.5562 (12.6° C.) |
| 65 | $CH_3$ | $CH_3$ | $CH_3$ | 4-$CHF_2O$—Ph | |
| 66 | $CH_3$ | $CH_3$ | $CH_3$ | 2-$NO_2$—Ph | |
| 67 | $CH_3$ | $CH_3$ | $CH_3$ | 3-$NO_2$—Ph | m.p. 85.5° C. |
| 68 | $CH_3$ | $CH_3$ | $CH_3$ | 4-$NO_2$—Ph | m.p. 83.8–88.1° C. |
| 69 | $CH_3$ | $CH_3$ | $CH_3$ | 4-Cl-3-$NO_2$—Ph | m.p. 101.6–103.3° C. |
| 70 | $CH_3$ | $CH_3$ | $CH_3$ | 4-$CH_3$-3-$NO_2$—Ph | nD 1.5650 (13.7° C.) |
| 71 | $CH_3$ | $CH_3$ | $CH_3$ | 2,4,6-$(CH_3)_3$—Ph | nD 1.5630 (18.5° C.) |
| 72 | $CH_3$ | $CH_3$ | $CH_3$ | 2,4,5-$(CH_3)_3$—Ph | |
| 73 | $CH_3$ | $CH_3$ | $CH_3$ | 2-CN-Ph | |
| 74 | $CH_3$ | $CH_3$ | $CH_3$ | 3-CN-Ph | nD 1.5665 (15.5° C.) |
| 75 | $CH_3$ | $CH_3$ | $CH_3$ | 4-CN-Ph | m.p. 97.1–98.6° C. |
| 76 | $CH_3$ | $CH_3$ | $CH_3$ | 2-$CH_3S$—Ph | |
| 77 | $CH_3$ | $CH_3$ | $CH_3$ | 3-$CH_3S$—Ph | |
| 78 | $CH_3$ | $CH_3$ | $CH_3$ | 4-$CH_3S$—Ph | m.p. 100.7–101.5° C. |
| 79 | $CH_3$ | $CH_3$ | $CH_3$ | 2-$CF_3S$—Ph | |
| 80 | $CH_3$ | $CH_3$ | $CH_3$ | 3-$CF_3S$—Ph | |
| 81 | $CH_3$ | $CH_3$ | $CH_3$ | 4-$CF_3S$—Ph | |
| 82 | $CH_3$ | $CH_3$ | $CH_3$ | 3-F-4-$CH_3S$—Ph | nD 1.5910 (19.0° C.) |
| 83 | $CH_3$ | $CH_3$ | $CH_3$ | 2-$N(CH_3)_2$—Ph | |
| 84 | $CH_3$ | $CH_3$ | $CH_3$ | 3-$N(CH_3)_2$—Ph | nD 1.5767 (13.7° C.) |
| 85 | $CH_3$ | $CH_3$ | $CH_3$ | 4-$N(CH_3)_2$—Ph | nD 1.5973 (19.5° C.) |
| 86 | $CH_3$ | $CH_3$ | $CH_3$ | 3-$PhCH_2O$—Ph | nD 1.5166 (19.0° C.) |
| 87 | $CH_3$ | $CH_3$ | $CH_3$ | Pyridin-2-yl | nD 1.5622 (16.8° C.) |
| 88 | $CH_3$ | $CH_3$ | $CH_3$ | Pyridin-3-yl | nD 1.5083 (17.2° C.) |
| 89 | $CH_3$ | $CH_3$ | $CH_3$ | Pyridin-4-yl | nD 1.4990 (17.3° C.) |
| 90 | $CH_3$ | $CH_3$ | $CH_3$ | Pyrazin-2-yl | m.p. 148.3–149.2° C. |
| 91 | $CH_3$ | $CH_3$ | $CH_3$ | Pyrazin-3-yl | |
| 92 | $CH_3$ | $CH_3$ | $CH_3$ | Naphthalen-2-yl | nD 1.6022 (26.9° C.) |
| 93 | $CH_3$ | $CH_3$ | $CH_3$ | Indan-5-yl | m.p. 91.7–93.6° C. |
| 94 | $CH_3$ | $CH_3$ | $CH_3$ | Tetralin-6-yl | m.p. 91.6–95.0° C. |
| 95 | $CH_3$ | $CH_3$ | $CH_3$ | Thiophen-2-yl | |
| 96 | $CH_3$ | $CH_3$ | $CH_3$ | 4-Br-thiophen-2-yl | |
| 97 | $CH_3$ | $CH_3$ | $C_2H_5$ | Ph | |
| 98 | $CH_3$ | $CH_3$ | $C_2H_5$ | 2-F—Ph | |
| 99 | $CH_3$ | $CH_3$ | $C_2H_5$ | 3-F—Ph | |
| 100 | $CH_3$ | $CH_3$ | $C_2H_5$ | 4-F—Ph | nD 1.5613 (16.5° C.) |
| 101 | $CH_3$ | $CH_3$ | $C_2H_5$ | 2,4-$F_2$—Ph | nD 1.5512 (13.3° C.) |
| 102 | $CH_3$ | $CH_3$ | $C_2H_5$ | 3,4-$F_2$—Ph | nD 1.5540 (14.3° C.) |
| 103 | $CH_3$ | $CH_3$ | $C_2H_5$ | 2,4,5-$F_3$—Ph | |
| 104 | $CH_3$ | $CH_3$ | $C_2H_5$ | 2-Cl—Ph | |
| 105 | $CH_3$ | $CH_3$ | $C_2H_5$ | 3-Cl—Ph | |
| 106 | $CH_3$ | $CH_3$ | $C_2H_5$ | 4-Cl—Ph | m.p. 66.5–70.2° C. |
| 107 | $CH_3$ | $CH_3$ | $C_2H_5$ | 2-I—Ph | |
| 108 | $CH_3$ | $CH_3$ | $C_2H_5$ | 3-I—Ph | |
| 109 | $CH_3$ | $CH_3$ | $C_2H_5$ | 4-I—Ph | |
| 110 | $CH_3$ | $CH_3$ | $C_2H_5$ | 2,4-$Cl_2$—Ph | |
| 111 | $CH_3$ | $CH_3$ | $C_2H_5$ | 3,4-$Cl_2$—Ph | m.p. 87.6–90.1° C. |
| 112 | $CH_3$ | $CH_3$ | $C_2H_5$ | 4-F-3-$CH_3$—Ph | m.p. 78.1–80.7° C. |
| 113 | $CH_3$ | $CH_3$ | $C_2H_5$ | 2-$CH_3$—Ph | |
| 114 | $CH_3$ | $CH_3$ | $C_2H_5$ | 3-$CH_3$—Ph | |
| 115 | $CH_3$ | $CH_3$ | $C_2H_5$ | 4-$CH_3$—Ph | |
| 116 | $CH_3$ | $CH_3$ | $C_2H_5$ | 3,4-$(CH_3)_2$—Ph | m.p. 92.6–98.9° C. |
| 117 | $CH_3$ | $CH_3$ | $C_2H_5$ | 2,5-$(CH_3)_2$—Ph | nD 1.5480 (22.3° C.) |
| 118 | $CH_3$ | $CH_3$ | $C_2H_5$ | 2-$CF_3$—Ph | |
| 119 | $CH_3$ | $CH_3$ | $C_2H_5$ | 3-$CF_3$—Ph | |
| 120 | $CH_3$ | $CH_3$ | $C_2H_5$ | 4-$CF_3$—Ph | |
| 121 | $CH_3$ | $CH_3$ | $C_2H_5$ | 2-$CH_3O$—Ph | |
| 122 | $CH_3$ | $CH_3$ | $C_2H_5$ | 3-$CH_3O$—Ph | |
| 123 | $CH_3$ | $CH_3$ | $C_2H_5$ | 4-$CH_3O$—Ph | |
| 124 | $CH_3$ | $CH_3$ | $C_2H_5$ | 2-$CF_3O$—Ph | |
| 125 | $CH_3$ | $CH_3$ | $C_2H_5$ | 3-$CF_3O$—Ph | |
| 126 | $CH_3$ | $CH_3$ | $C_2H_5$ | 4-$CF_3O$—Ph | |
| 127 | $CH_3$ | $CH_3$ | $C_2H_5$ | 2-CN—Ph | |
| 128 | $CH_3$ | $CH_3$ | $C_2H_5$ | 3-CN—Ph | |
| 129 | $CH_3$ | $CH_3$ | $C_2H_5$ | 4-CN—Ph | |
| 130 | $CH_3$ | $CH_3$ | $C_2H_5$ | 2-$NO_2$—Ph | |
| 131 | $CH_3$ | $CH_3$ | $C_2H_5$ | 3-$NO_2$—Ph | |
| 132 | $CH_3$ | $CH_3$ | $C_2H_5$ | 4-$NO_2$—Ph | |
| 133 | $CH_3$ | $CH_3$ | $C_2H_5$ | 2-$CH_3S$—Ph | |
| 134 | $CH_3$ | $CH_3$ | $C_2H_5$ | 3-$CH_3S$—Ph | |
| 135 | $CH_3$ | $CH_3$ | $C_2H_5$ | 4-$CH_3S$—Ph | |
| 136 | $CH_3$ | $CH_3$ | $C_2H_5$ | 2-$CF_3S$—Ph | |
| 137 | $CH_3$ | $CH_3$ | $C_2H_5$ | 3-$CF_3S$—Ph | |
| 138 | $CH_3$ | $CH_3$ | $C_2H_5$ | 4-$CF_3S$—Ph | |
| 139 | $CH_3$ | $CH_3$ | $C_2H_5$ | Pyridin-2-yl | |
| 140 | $CH_3$ | $CH_3$ | $C_2H_5$ | Pyridin-3-yl | |
| 141 | $CH_3$ | $CH_3$ | $C_2H_5$ | Pyridin-4-yl | |
| 142 | $CH_3$ | $CH_3$ | $C_2H_5$ | Pyrazin-2-yl | |
| 143 | $CH_3$ | $CH_3$ | $C_2H_5$ | Pyrazin-3-yl | |
| 144 | $CH_3$ | $CH_3$ | $C_2H_5$ | Naphthalen-2-yl | |

TABLE 3-continued (wherein Ph = a phenyl group; $R^3$ = $CH_3$ and Y = O in the general formula (1))

General formula (I)

$$\text{Ph-CH}_2\text{O}-\overset{R^3}{\underset{}{C}}=N-N=C(R^4)(R^5)$$
with N—CO—YR² and OR¹ substituents

| No | $R^1$ | $R^2$ | $R^4$ | $R^5$ | Physical property |
|---|---|---|---|---|---|
| 145 | $CH_3$ | $CH_3$ | $C_2H_5$ | Indan-5-yl | |
| 146 | $CH_3$ | $CH_3$ | $C_2H_5$ | Tetralin-6-yl | |
| 147 | $CH_3$ | $CH_3$ | $C_2H_5$ | Thiopen-2-yl | |
| 148 | $CH_3$ | $CH_3$ | $C_2H_5$ | 4-Br-thiophen-2-yl | |
| 149 | $C_2H_5$ | $CH_3$ | $CH_3$ | Ph | |
| 150 | $C_2H_5$ | $CH_3$ | $CH_3$ | 2-F—Ph | |
| 151 | $C_2H_5$ | $CH_3$ | $CH_3$ | 3-F—Ph | |
| 152 | $C_2H_5$ | $CH_3$ | $CH_3$ | 4-F—Ph | nD 1.5578 (17.5° C.) |
| 153 | $C_2H_5$ | $CH_3$ | $CH_3$ | 2,4-$F_2$—Ph | nD 1.5419 (22.4° C.) |
| 154 | $C_2H_5$ | $CH_3$ | $CH_3$ | 3,4-$F_2$—Ph | nD 1.5530 (16.6° C.) |
| 155 | $C_2H_5$ | $CH_3$ | $CH_3$ | 2,6-$F_2$—Ph | nD 1.5463 (14.0° C.) |
| 156 | $C_2H_5$ | $CH_3$ | $CH_3$ | 2,4,5-$F_3$—Ph | |
| 157 | $C_2H_5$ | $CH_3$ | $CH_3$ | 2-Cl—Ph | |
| 158 | $C_2H_5$ | $CH_3$ | $CH_3$ | 3-Cl—Ph | nD 1.5777 (18.9° C.) |
| 159 | $C_2H_5$ | $CH_3$ | $CH_3$ | 4-Cl—Ph | nD 1.5767 (15.8° C.) |
| 160 | $C_2H_5$ | $CH_3$ | $CH_3$ | 2,4-$Cl_2$—Ph | Paste |
| 161 | $C_2H_5$ | $CH_3$ | $CH_3$ | 3,4-$Cl_2$—Ph | |
| 162 | $C_2H_5$ | $CH_3$ | $CH_3$ | 2-I—Ph | |
| 163 | $C_2H_5$ | $CH_3$ | $CH_3$ | 3-I—Ph | |
| 164 | $C_2H_5$ | $CH_3$ | $CH_3$ | 4-I—Ph | |
| 165 | $C_2H_5$ | $CH_3$ | $CH_3$ | 2-$CH_3$—Ph | |
| 166 | $C_2H_5$ | $CH_3$ | $CH_3$ | 3-$CH_3$—Ph | nD 1.5644 (22.2° C.) |
| 167 | $C_2H_5$ | $CH_3$ | $CH_3$ | 4-$CH_3$—Ph | |
| 168 | $C_2H_5$ | $CH_3$ | $CH_3$ | 2-$CH_3O$—Ph | nD 1.5529 (23.0° C.) |
| 169 | $C_2H_5$ | $CH_3$ | $CH_3$ | 3-$CH_3O$—Ph | |
| 170 | $C_2H_5$ | $CH_3$ | $CH_3$ | 4-$CH_3O$—Ph | |
| 171 | $C_2H_5$ | $CH_3$ | $CH_3$ | 3,4-$(CH_3O)_2$—Ph | nD 1.5689 (17.6° C.) |
| 172 | $C_2H_5$ | $CH_3$ | $CH_3$ | 2-$C_2H_5$—Ph | |
| 173 | $C_2H_5$ | $CH_3$ | $CH_3$ | 4-$C_2H_5$—Ph | m.p. 66.2–70.1° C. |
| 174 | $C_2H_5$ | $CH_3$ | $CH_3$ | 2-$NO_2$—Ph | |
| 175 | $C_2H_5$ | $CH_3$ | $CH_3$ | 3-$NO_2$—Ph | |
| 176 | $C_2H_5$ | $CH_3$ | $CH_3$ | 4-$NO_2$—Ph | nD 1.5862 (16.2° C.) |
| 177 | $C_2H_5$ | $CH_3$ | $CH_3$ | 2-CN—Ph | |
| 178 | $C_2H_5$ | $CH_3$ | $CH_3$ | 3-CN—Ph | |
| 179 | $C_2H_5$ | $CH_3$ | $CH_3$ | 4-CN—Ph | |
| 180 | $C_2H_5$ | $CH_3$ | $CH_3$ | 2-$CF_3$—Ph | |
| 181 | $C_2H_5$ | $CH_3$ | $CH_3$ | 3-$CF_3$—Ph | |
| 182 | $C_2H_5$ | $CH_3$ | $CH_3$ | 4-$CF_3$—Ph | |
| 183 | $C_2H_5$ | $CH_3$ | $CH_3$ | 2-$CHF_2$—Ph | |
| 184 | $C_2H_5$ | $CH_3$ | $CH_3$ | 3-$CHF_2$—Ph | |
| 185 | $C_2H_5$ | $CH_3$ | $CH_3$ | 4-$CF_3O$—Ph | m.p. 87.3–88.9° C. |
| 186 | $C_2H_5$ | $CH_3$ | $CH_3$ | 2-$CH_3S$—Ph | |
| 187 | $C_2H_5$ | $CH_3$ | $CH_3$ | 3-$CH_3S$—Ph | |
| 188 | $C_2H_5$ | $CH_3$ | $CH_3$ | 4-$CH_3S$—Ph | m.p. 104.6–106.5° C. |
| 189 | $C_2H_5$ | $CH_3$ | $CH_3$ | 2-$CF_3S$—Ph | |
| 190 | $C_2H_5$ | $CH_3$ | $CH_3$ | 3-$CF_3S$—Ph | |
| 191 | $C_2H_5$ | $CH_3$ | $CH_3$ | 4-$CF_3S$—Ph | |
| 192 | $C_2H_5$ | $CH_3$ | $CH_3$ | 3-Br—Ph | Paste |
| 193 | $C_2H_5$ | $CH_3$ | $CH_3$ | 3-$CF_3O$—Ph | Paste |
| 194 | $C_2H_5$ | $CH_3$ | $CH_3$ | Pyridin-2-yl | nD 1.5618 (21.2° C.) |
| 195 | $C_2H_5$ | $CH_3$ | $CH_3$ | Pyridin-3-yl | |
| 196 | $C_2H_5$ | $CH_3$ | $CH_3$ | Pyridin-4-yl | |
| 197 | $C_2H_5$ | $CH_3$ | $CH_3$ | Pyrazin-2-yl | nD 1.5618 (21.2° C.) |
| 198 | $C_2H_5$ | $CH_3$ | $CH_3$ | Pyrazin-3-yl | |
| 199 | $C_2H_5$ | $CH_3$ | $CH_3$ | Naphthalen-2-yl | |
| 200 | $C_2H_5$ | $CH_3$ | $CH_3$ | Indan-5-yl | nD 1.5768 (23.1° C.) |
| 201 | $C_2H_5$ | $CH_3$ | $CH_3$ | Tetralin-6-yl | nD 1.5757 (23.2° C.) |
| 202 | $C_2H_5$ | $CH_3$ | $CH_3$ | Thiophen-2-yl | |
| 203 | $C_2H_5$ | $CH_3$ | $CH_3$ | 5-Br-thiophen-2-yl | nD 1.5826 (22.9° C.) |
| 204 | $CH_3$ | $C_2H_5$ | $CH_3$ | Ph | |
| 205 | $CH_3$ | $C_2H_5$ | $CH_3$ | 2-F—Ph | |
| 206 | $CH_3$ | $C_2H_5$ | $CH_3$ | 3-F—Ph | |
| 207 | $CH_3$ | $C_2H_5$ | $CH_3$ | 4-F—Ph | |
| 208 | $CH_3$ | $C_2H_5$ | $CH_3$ | 2,4-$F_2$—Ph | |
| 209 | $CH_3$ | $C_2H_5$ | $CH_3$ | 3,4-$F_2$—Ph | |
| 210 | $CH_3$ | $C_2H_5$ | $CH_3$ | 2,6-$F_2$—Ph | |
| 211 | $CH_3$ | $C_2H_5$ | $CH_3$ | 2,4,5-$F_3$—Ph | |
| 212 | $CH_3$ | $C_2H_5$ | $CH_3$ | 2-Cl—Ph | |
| 213 | $CH_3$ | $C_2H_5$ | $CH_3$ | 3-Cl—Ph | |
| 214 | $CH_3$ | $C_2H_5$ | $CH_3$ | 4-Cl—Ph | |
| 215 | $CH_3$ | $C_2H_5$ | $CH_3$ | 2,4-$Cl_2$—Ph | |
| 216 | $CH_3$ | $C_2H_5$ | $CH_3$ | 3,4-$Cl_2$—Ph | |
| 217 | $CH_3$ | $C_2H_5$ | $CH_3$ | 2-I—Ph | |
| 218 | $CH_3$ | $C_2H_5$ | $CH_3$ | 3-I—Ph | |
| 219 | $CH_3$ | $C_2H_5$ | $CH_3$ | 4-I—Ph | |
| 220 | $CH_3$ | $C_2H_5$ | $CH_3$ | 2-$CH_3$—Ph | |
| 221 | $CH_3$ | $C_2H_5$ | $CH_3$ | 3-$CH_3$—Ph | |
| 222 | $CH_3$ | $C_2H_5$ | $CH_3$ | 4-$CH_3$—Ph | |
| 223 | $CH_3$ | $C_2H_5$ | $CH_3$ | 2-$CH_3O$—Ph | |
| 224 | $CH_3$ | $C_2H_5$ | $CH_3$ | 3-$CH_3O$—Ph | |
| 225 | $CH_3$ | $C_2H_5$ | $CH_3$ | 4-$CH_3O$—Ph | |
| 226 | $CH_3$ | $C_2H_5$ | $CH_3$ | 3,4-$(CH_3O)_2$—Ph | |
| 227 | $CH_3$ | $C_2H_5$ | $CH_3$ | 2-$C_2H_5$-Ph | |
| 228 | $CH_3$ | $C_2H_5$ | $CH_3$ | 4-$C_2H_5$-Ph | |
| 229 | $CH_3$ | $C_2H_5$ | $CH_3$ | 2-$NO_2$—Ph | |
| 230 | $CH_3$ | $C_2H_5$ | $CH_3$ | 3-$NO_2$—Ph | |
| 231 | $CH_3$ | $C_2H_5$ | $CH_3$ | 4-$NO_2$—Ph | |
| 232 | $CH_3$ | $C_2H_5$ | $CH_3$ | 2-CN—Ph | |
| 233 | $CH_3$ | $C_2H_5$ | $CH_3$ | 3-CN—Ph | |
| 234 | $CH_3$ | $C_2H_5$ | $CH_3$ | 4-CN—Ph | |
| 235 | $CH_3$ | $C_2H_5$ | $CH_3$ | 2-$CF_3$—Ph | |
| 236 | $CH_3$ | $C_2H_5$ | $CH_3$ | 3-$CF_3$—Ph | |
| 237 | $CH_3$ | $C_2H_5$ | $CH_3$ | 4-$CF_3$—Ph | |
| 238 | $CH_3$ | $C_2H_5$ | $CH_3$ | 2-$CHF_2O$—Ph | |
| 239 | $CH_3$ | $C_2H_5$ | $CH_3$ | 3-$CHF_2O$—Ph | |
| 240 | $CH_3$ | $C_2H_5$ | $CH_3$ | 4-$CHF_2O$—Ph | |
| 241 | $CH_3$ | $C_2H_5$ | $CH_3$ | 2-$CH_3S$—Ph | |
| 242 | $CH_3$ | $C_2H_5$ | $CH_3$ | 3-$CH_3S$—Ph | |
| 243 | $CH_3$ | $C_2H_5$ | $CH_3$ | 4-$CH_3S$—Ph | |
| 244 | $CH_3$ | $C_2H_5$ | $CH_3$ | 2-$CF_3S$—Ph | |
| 245 | $CH_3$ | $C_2H_5$ | $CH_3$ | 3-$CF_3S$—Ph | |
| 246 | $CH_3$ | $C_2H_5$ | $CH_3$ | 4-$CF_3S$—Ph | |
| 247 | $CH_3$ | $C_2H_5$ | $CH_3$ | Pyridin-2-yl | |
| 248 | $CH_3$ | $C_2H_5$ | $CH_3$ | Pyridin-3-yl | |
| 249 | $CH_3$ | $C_2H_5$ | $CH_3$ | Pyridin-4-yl | |
| 250 | $CH_3$ | $C_2H_5$ | $CH_3$ | Pyrazin-2-yl | |
| 251 | $CH_3$ | $C_2H_5$ | $CH_3$ | Pyrazin-3-yl | |
| 252 | $CH_3$ | $C_2H_5$ | $CH_3$ | Napthalen-2-yl | |
| 253 | $CH_3$ | $C_2H_5$ | $CH_3$ | Indan-5-yl | |
| 254 | $CH_3$ | $C_2H_5$ | $CH_3$ | Tetralin-6-yl | |

TABLE 3-continued (wherein Ph = a phenyl group; $R^3 = CH_3$ and $Y = 0$ in the general formula (I))

General formula (I)

$$\underset{\substack{|\\OR^1}}{\underset{|}{\overset{R^3}{\underset{|}{C}}}}\,\,\,\text{(Ph)}\text{-}CH_2O\text{-}C=N\text{-}N=C(R^4)(R^5)\\ \text{N-CO-YR}^2$$

| No  | $R^1$ | $R^2$    | $R^4$  | $R^5$           | Physical property |
|-----|-------|----------|--------|-----------------|-------------------|
| 255 | $CH_3$ | $C_2H_5$ | $CH_3$ | Thiophen-2-yl    |                   |
| 256 | $CH_3$ | $C_2H_5$ | $CH_3$ | 4-Br-thiophen-2-yl |                 |

Table 4 shows NMR data of the compounds having a physical property expressed by the word "$^1$H-NMR or paste" in Table 3.

TABLE 4

| No | $^1$H-NMR data [300 NMz, $CDCl_3$/TMs, δ value (ppm)] |
|----|-------------------------------------------------------|
| 1  | 2.157 (s, 3H), 2.261 (s, 3H), 3.794 (s, 3H), 5.376 (s, 2H), 7.35–7.45 (m, 6H), 7.52–7.58 (m, 1H), 7.77–7.84 (m, 2H), 8.14 (br, 1H). |
| 2  | 2.170 (s, 3H), 2.247 (s, 3H), 3.781 (s, 3H), 5.369 (s, 2H), 7.03–7.12 (m, 1H), 7.28–7.42 (m, 4H), 7.5–7.58 (m, 3H), 8.28 (br, 1H). |
| 3  | 2.156 (s, 3H), 2.247 (s, 3H), 3.792 (s, 3H), 5.372 (s, 2H), 7.3–7.42 (m, 5H), 7.52–7.58 (m, 1H), 7.72–7.78 (d, 2H), 8.08 (br, 1H). |
| 4  | 2.209 (s, 3H), 2.333 (s, 3H), 3.790 (s, 3H), 5.391 (s, 2H), 7.37–7.43 (m, 3H), 7.51–7.58 (m, 2H), 8.12 (br, 1H), H 8.14–8.26 (m, 2H), 8.62–8.67 (m, 1H). |
| 5  | 2.168 (s, 3H), 2.237 (s, 3H), 3.784 (s, 3H), 5.367 (s, 2H), 7.1–7.2 (dd, 1H), 7.36–7.43 (m, 3H), 7.47–7.58 (m, 2H), 7.65–7.74 (m, 1H), 8.123 (br, 1H). |
| 6  | 2.101 (s, 3H), 2.185 (s, 3H), 3.796 (s, 3H), 5.352 (s, 2H), 7.22–7.3 (m, 2H), 7.37–7.44 (m, 4H), 7.52–7.58 (m, 1H), 8.02 (br, 1H). |
| 7  | 2.133 (s, 3H), 2.212 (s, 3H), 2.279 (s, 3H), 2.286 (s, 3H), 3.792 (s, 3H), 5.363 (s, 2H), 7.145 (d, 1H), 7.36–7.42 (m, 3H), 7.48–7.59 (m, 3H), 8.22 (br, 1H). |
| 192 | 1.24 (t, 3H, J=7Hz), 2.21 (s, 3H), 2.29 (s, 3H), 3.80 (s, 3H), 3.99 (q, 2H, J=7Hz), 5.33 (s, 2H), 7.23–7.31 (m, 1H), 7.32–7.42 (m, 4H), 7.47–7.58 (m, 1H), 7.73–7.78 (m, 1H), 8.00 (t, 1H, J=1.9Hz). |
| 193 | 1.24 (t, 3H, J=7Hz), 2.22 (s, 3H), 2.32 (s, 3H), 3.79 (s, 3H), 3.99 (q, 2H, J=7Hz), 5.34 (s, 2H), 7.23–7.26 (m, 1H), 7.45–7.53 (m, 4H), 7.51–7.61 (m, 1H), 7.70–7.80 (m, 2H). |

Typical examples of the present invention are described below, but they should not be construed as limiting the scope of the invention.

EXAMPLE 1

1-1. Production of N-2-methylphenylhydroxyamine

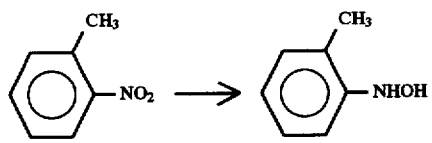

To 400 ml of ethanol were added 70 g (0.51 mole) of o-nitrotoluene and 66.8 g of zinc, and 300 ml of an aqueous solution of 30 g of ammonium chloride was slowly dropped into the resulting mixture with stirring at a reaction temperature of 45°–55° C.

After completion of the dropping, the reaction mixture was filtered at room temperature and the filtrate was concentrated under reduced pressure. The resulting residue was added to 300 ml of water and the desired compound was extracted with ethyl acetate. The extracted solution was washed with a saturated aqueous sodium chloride solution and dried over sodium sulfate, after which the solvent was distilled off under reduced pressure to obtain 47 g (yield 74%) of the desired compound.

The N-2-methylphenylhydroxyamine obtained was used in the subsequent reaction without purification.

1-2. Production of methyl N-hydroxy-N-2-methylphenylcarbamate

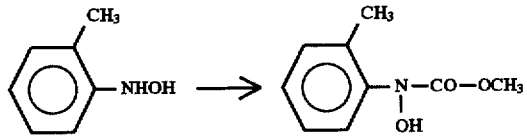

To 60 ml of tetrahydrofuran were added 5.9 g (0.048 mole) of the N-2-methylphenylhydroxyamine obtained in 1-1 and 3.9 g of triethylamine, and 40 ml of a solution of 3.6 g of methyl chlorocarbonate in tetrahydrofuran was added dropwise at 0° C. over a period of 40 minutes. The reaction was carried out with stirring at 0° C. for another 30 minutes.

After completion of the reaction, the reaction mixture was filtered at room temperature. The resulting filtrate was poured into 40 ml of water and the desired compound was extracted with ethyl acetate. The extracted solution was washed with a saturated aqueous sodium chloride solution and dried over sodium sulfate, after which the solvent was distilled off under reduced pressure. The resulting residue was purified by a silica gel column chromatography to obtain 6.0 g of the desired compound.

Physical property:

NMR [$CDCl_3$/TMS, δ values (ppm)] 2.35 (s, 3H), 3.74 (s, 3H), 7.20–7.30 (m, 3H), 7.24–7.29 (m, 1H), 9.20–9.27 (br, 1H).

Yield: 69%.

1-3. Production of methyl N-ethoxy-N-2-methylphenylcarbamate

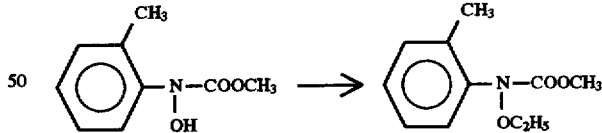

To 30 ml of acetone were added 2.25 g (0.012 mole) of the methyl N-hydroxy-N-2-methylphenylcarbamate obtained in 1-2, 2.1 g of anhydrous potassium carbonate and 1.6 g of ethyl bromide, and the reaction was carried out with heating under reflux for 3 hours.

After completion of the reaction, the reaction mixture was poured into 40 ml of water and the desired compound was extracted with ethyl acetate. The extracted solution was washed with a saturated aqueous sodium chloride solution and dried over sodium sulfate, after which the solvent was distilled off under reduced pressure. The resulting residue was purified by a silica gel column chromatography to obtain 1.6 g of the desired compound.

Physical property:

NMR [CDCl₃/TMS, δ values (ppm)] 1.23 (t, 3H, J=7.2 Hz), 3.77 (s, 3H), 3.96 (q, 2H, J=7.2 Hz), 7.19–7.32 (m, 4H).
Yield: 62%.

Methyl N-2-methylphenyl-N-methoxycarbamate was produced in a similar manner as above.
Physical property:
NMR [CDCl₃/TMS, δ values (ppm)] 2.29 (s, 3H), 3.73 (s, 3H), 3.78 (s, 3H), 7.20–7.32 (m, 4H).

1-4. Production of methyl N-2-bromomethylphenyl-N-ethoxycarbamate

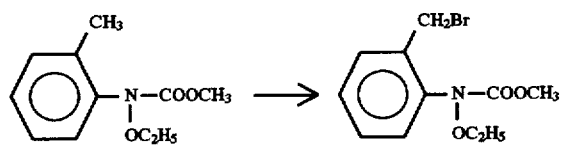

To 20 ml of carbon tetrachloride were added 1.6 g (0.076 mole) of the methyl N-ethoxy-N-2-methyl-phenylcarbamate, 1.4 g of N-bromosuccinimide and a small amount of azobis(isobutyronitrile), and the reaction was carried out with heating under reflux for 5 hours under light irradiation (TOKI REFLIGHT, Model LC-107).

After completion of the reaction, 30 ml of water was added to the reaction mixture, and the organic layer was separated, washed with a saturated aqueous sodium chloride solution and dried over sodium sulfate. Then, the solvent was distilled off under reduced pressure and the resulting residue was purified by a silca gel column chromatography to obtain 1.5 g of the desired compound.
Physical property: nD 1.5460 (18.5° C.).
Yield: 68%.

Methyl N-2-bromomethylphenyl-N-methoxycarbamate was produced in a similar manner as above.
Physical property: nD 1.5570 (18.5° C.).

1-5. Production of methyl N-ethoxy-N-[2-[1-[N'-{1-(3-chlorophenyl)ethylidene}hydrazono]ethyloxymethyl]phenyl]carbamate (compound No. 158)

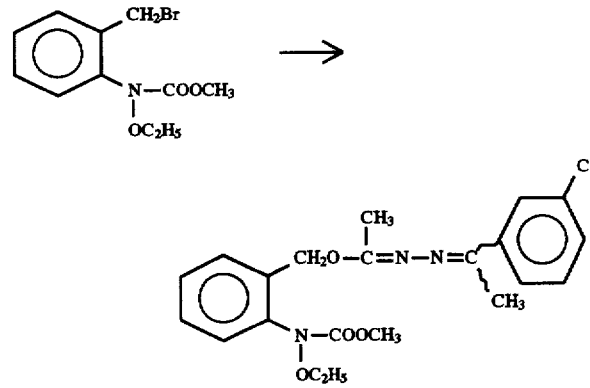

To 10 ml of N,N-dimethylformamide (DMF) were added 0.2 g (1.9 mmoles) of potassium t-butoxide and 0.4 g (1.9 mmoles) of 1-acetyl-2-{1-(3-chlorophenyl)ethylidene}hydrazine, and the reaction was carried out at room temperature for 10 minutes. Then, the reaction mixture was slowly dropped into 15 ml of a solution of 0.5 g (1.7 mmoles) of methyl N-{2-(bromomethyl)phenyl}-N-ethoxycarbamate in DMF, and the resulting mixture was subjected to reaction at room temperature for 2 hours.

After completion of the reaction, the reaction mixture was poured into water and the desired compound was extracted with ethyl acetate. The extracted solution was washed with a saturated aqueous sodium chloride solution, dried over anhydrous sodium sulfate, and then distilled under reduced pressure to remove the solvent. The resulting residue was purified by a silica gel column chromatography to obtain 0.47 g of the desired compound.
Physical property: nD 1.5777 (18.9° C.).
Yield: 65%.

EXAMPLE 2

Production of methyl N-[2-[1-[N'-{1-(2,4-difluorophenyl)-1-propylidene}hydrazono]ethyloxymethyl]phenyl]-N-methoxycarbamate (compound No. 101)

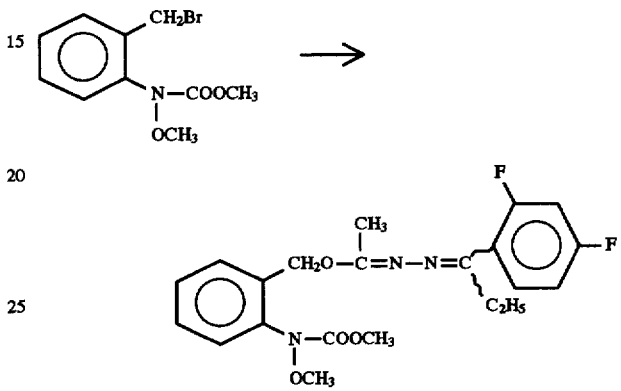

To 10 ml of DMF were added 0.5 g (1.8 mmoles) of 1-acetyl-2-[1-(2,4-difluorophenyl)-1-propylidene]hydrazine and 0.13 g (85%, 2.0 mmoles) of potassium hydroxide powder, and the reaction was carried out at room temperature for 10 minutes. Then, the reaction mixture was slowly dropped into 15 ml of a solution of 0.5 g (1.8 mmoles) of methyl N-{2-(bromomethyl)phenyl}-N-methoxycarbamate in DMF, and the resulting mixture was subjected to reaction at room temperature for 3 hours.

After completion the reaction, the reaction mixture was poured into water and the desired compound was extracted with ethyl acetate. The extracted solution was washed with a saturated aqueous sodium chloride solution, dried over anhydrous sodium sulfate, and then distilled under reduced pressure to remove the solvent. The resulting residue was purified by a silica gel column chromatography to obtain 0.55 g of the desired compound.
Physical property: nD 1.5512 (13.3° C.).
Yield: 65%.

EXAMPLE 3

3-1. Production of 2-{2-(bromomethyl)phenyl}-1,4,2-dioxazolidin-3-one (compound No. V-2)

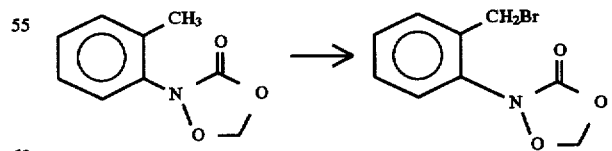

To 50 ml of benzene were added 2.0 g (11 mmoles) of 2-(2-methylphenyl)-1,4,2-dioxazolidin-3-one, 2.0 g (11 mmoles) of N-bromosuccinimide and a small amount of azobisisobutyronitrile, and the reaction was carried out with heating under reflux and light irradiation (TOKI REFLIGHT, Model LC-107, 100 W).

After completion of the reaction, the reaction mixture was cooled to room temperature and poured into water, and the organic layer was separated, washed with a saturated aqueous sodium chloride solution, dried over anhydrous sodium sulfate, and then distilled under reduced pressure to remove the solvent. The resulting residue was purified by a silica gel column chromatography to obtain 2.1 g of the desired compound.

Physical property: paste. Yield: 72%.

¹H-NMR [200 MHz, TMS/CDCl₃, δ values (ppm)] 4.62 (s, 2H), 5.76 (s, 2H), 7.39–7.48 (m, 3H), 7.49–7.56 (m,1H).

3-2. Production of 2-[2-[1-[N'-{1-(4-chlorophenyl) ethylidene}hydrazono]ethoxymethyl]phenyl]-1,4,2-dioxazolidin-3-one (compound No. 19)

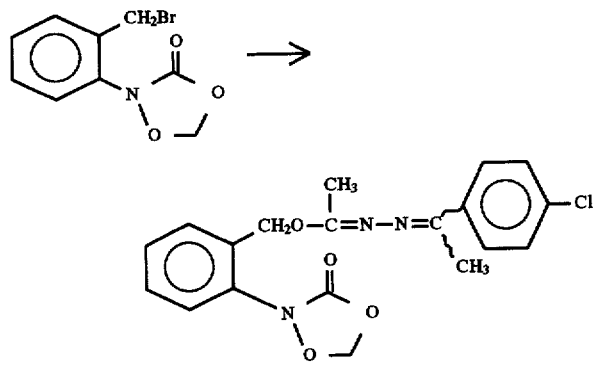

In 20 ml of DMF was suspended 0.11 g (62.4% in oil, 2.8 mmoles) of sodium hydride, after which 0.6 g (2.8 mmoles) of 1-acetyl-2-{1-(4-chlorophenyl)ethylidene}hydrazine was added to the suspension and the reaction was carried out at room temperature for 10 minutes. Then, 5 ml of a solution of 0.6 g (2.3 mmol) of 2-{2-(bromomethyl)phenyl}-1,4,2-dioxazolidin-3-one in DMF was slowly dropped into the reaction mixture, and the resulting mixture was subjected to reaction for 2 hours.

After completion of the reaction, the reaction mixture was poured into water and the desired compound was extracted with ethyl acetate. The extracted solution was washed with a saturated aqueous sodium chloride solution, dried over anhydrous sodium sulfate, and then distilled under reduced pressure to remove the solvent. The resulting residue was purified by a silica gel column chromatography to obtain 0.58 g of the desired compound.

Physical property: paste. Yield: 64%.

H-NMR [300 MHz, TMS/CDCl₃, δ values (ppm)] 2.23 (s, 3H), 2.29 , (s, 3H), 5.42 (s, 2H), 5.72 (s, 2H), 7.35 (d, 2H, J=4.3 Hz), 7.40–7.49 (m, 3H), 7.50–7.56 (m, 1H), 7.57–7.61 (m, 1H), 7.78 (d, 2H, J=4.3 Hz).

3-3. Production of methyl N-[2-[1-[N'-{1-(4-chlorophenyl) ethylidene}hydrazono]ethyloxymethyl]phenyl]-N-hydroxycarbamate (compound No. 3)

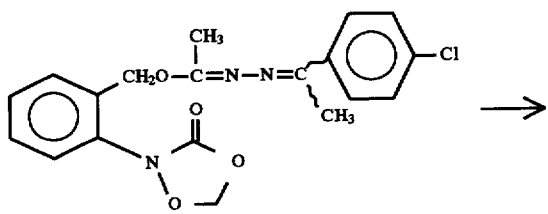

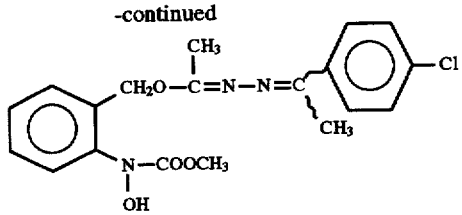

To 20 ml of a methanolic solution of 0.08 g (1.5 mmoles) of sodium methoxide was added 0.5 g (1.3 mmoles) of 2-[2-[1-[N'-{1-(4-chlorophenyl)ethylidene}hydrazono] ethyloxymethyl]phenyl]-1,4,2-dioxazolidin-3-one, and the reaction was carried out at room temperature for 2 hours.

After completion of the reaction, the reaction mixture was poured into water and the desired compound was extracted with ethyl acetate. The extracted solution was washed with a saturated aqueous sodium chloride solution, dried over anhydrous sodium sulfate, and then distilled under reduced pressure to remove the solvent. The resulting residue was purified by a silica gel column chromatography to obtain 0.48 g of the desired compound.

Physical property: m.p. 120.8°–127.5° C.

Yield: 96%.

3-4. Production of methyl N-[2-[1-[N'-{1-(4-chlorophenyl) ethylidene}hydrazono]ethyloxymethyl]phenyl]-N-methoxycarbamate (compound No. 22)

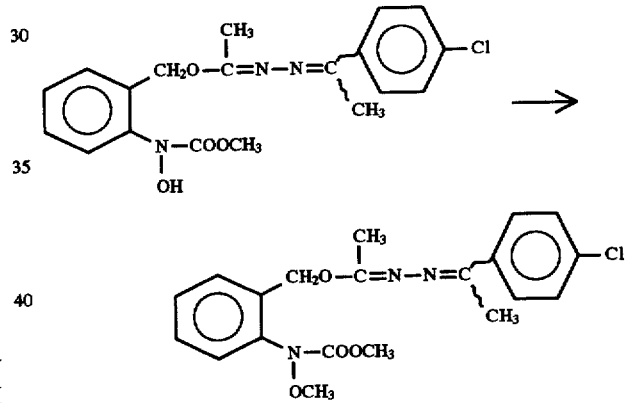

To 20 ml of acetone were added 0.4 g (1.0 mmole) of methyl N-[2-[1-[N'-{1-(4-chlorophenyl) ethylidene}hydrazono]ethyloxymethyl]phenyl]-N-hydroxycarbamate, 0.17 g (1.2 moles) of potassium carbonate and 0.17 g (1.2 mmoles) of methyl iodide, and the reaction was carried out with heating under reflux for 3 hours.

After completion of the reaction, the reaction mixture was poured into water and the desired compound was extracted with ethyl acetate. The extracted solution was washed with a saturated aqueous sodium chloride solution, dried over anhydrous sodium sulfate, and then distilled under reduced pressure to remove the solvent. The resulting residue was purified by a silica gel column chromatography to obtain 0.48 g of the desired compound.

Physical property: m.p. 64.2°–65.2° C.

Yield: 97%.

EXAMPLE 4

4-1. Production of 2-[2-[1-{1-(3-fluorophenyl) ethylidene}hydrazono]ethyloxymethyl]phenyl]-1,4,2-dioxazolidin-3-one (compound No. VI-7)

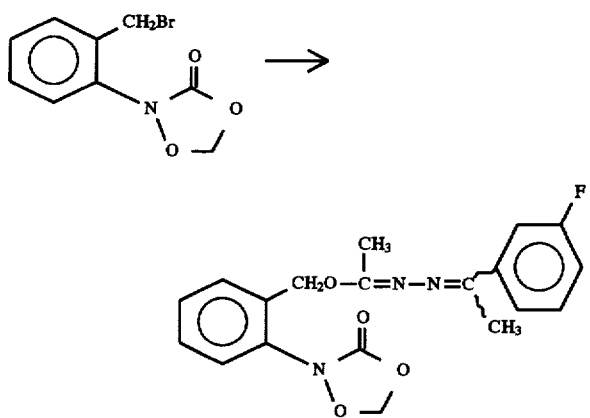

To 10 ml of N,N-dimethylformamide was added 0.3 g (1.6 mmoles) of 1-acetyl-2-{1-(3-fluorophenyl)ethylidene}hydrazine, and then to the resultant solution was added 0.18 g (1.6 mmoles) of potassium t-butoxide. The resultant mixture was stirred at room temperature for 10 minutes. To the thus prepared mixture was added 0.3 g (1.2 moles) of 2-{2-(bromomethyl)phenyl}-1,4,2-dioxazolidin-3-one, and the resultant mixture was subjected to reaction at room temperature for 4 hours.

After completion of the reaction, the reaction mixture was poured into water and the desired compound was extracted with ethyl acetate. The extracted solution was washed with a saturated aqueous sodium chloride solution, dried over anhydrous sodium sulfate, and then distilled under reduced pressure to remove the solvent. The resulting residue was purified by a silica gel column chromatography to obtain 0.18 g of the desired compound.

Yield: 42%

$^1$H-NMR [300 MHz, CDCl$_3$/TMS, δ values (ppm)] 2.239 (s, 3H), 2.298 (s, 3H), 5.431 (s, 2H), 5.716 (s, 2H), 7.03–7.12 (m, 1H), 7.3–7.65 (m, 7H).

4-2. Production of methyl N-[2-[1-N'-{1-(3-fluorophenyl)ethylidene}hydrazono]ethyloxymethyl]phenyl]-N-hydroxycarbamate (compound No. 2)

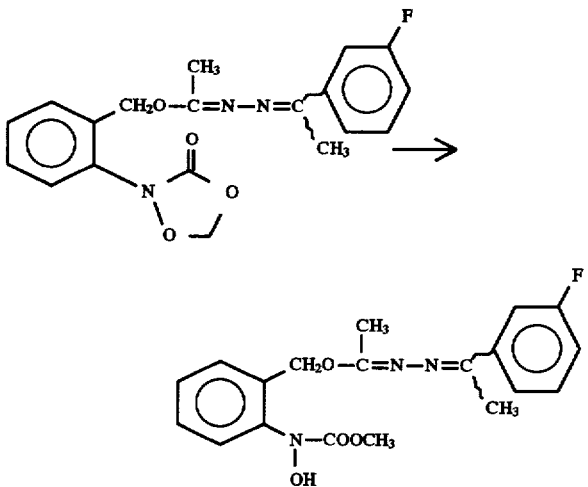

0.15 Grams (0.4 mmole) of 2-[2-[1-[N'-{1-(3-fluorophenyl)ethyliden}hydrazono]ethyloxymethyl]phenyl]-1,4,2-dioxazolidin-3-one was dissolved in 5 ml of methanol, and 0.03 g (0.56 mmole) of sodium methoxide was added to the resultant solution. The reaction was carried out at room temperature for 18 hours.

After completion of the reaction, the reaction mixture was poured into water and the desired compound was extracted with ethyl acetate. The extracted solution was washed with a saturated aqueous sodium chloride solution, dried over anhydrous sodium sulfate, and then distilled under reduced pressure to remove the solvent. The resulting residue was purified by a silica gel column chromatography to obtain 0.11 g of the desired compound.

Yield: 74%.

$^1$H-NMR [300 MHz, CDCl$_3$/TMS, δ values (ppm)] 2.170 (s, 3H), 2.247 (s, 3H), 3.781 (s, 3H), 5.369 (s, 2H), 7.03–7.12 (m, 1H), 7.28–7.42 (m, 4H), 7.5–7.58 (m, 3H), 8.28 (br, 1H).

4-3. Production of methyl N-[2-[1-[N'-{1-(3-fluorophenyl)ethylidene}hydrazono]ethyloxylmethyl]phenyl]-N-methoxycarbamate (compound No. 8)

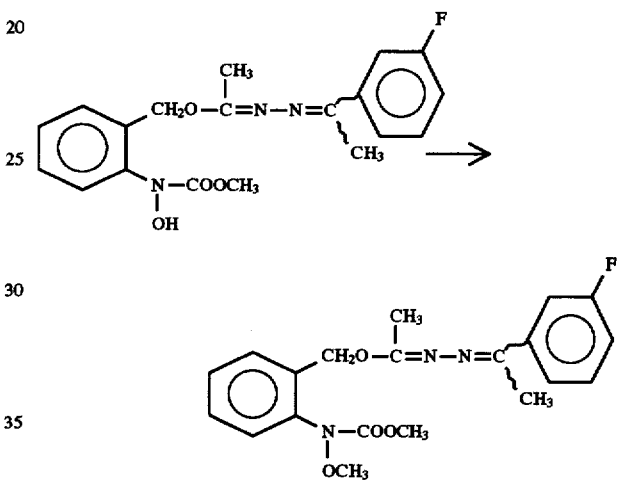

The desired compound was produced in a similar manner to that for Example 3-3 by using the compound obtained in 4-2 mentioned above as a starting material.

Physical property: nD 1.5654 (19.0° C.)

Yield: 94%

The N-substituted phenylcarbamic acid derivatives of the general formula (I) of the present invention are useful as agricultural and horticultural fungicides and are very effective in controlling various diseases, for example, rice blast (*Pyricularia oryzae*), rice sheath blight (*Rhizoctonia solani*), rice helminthosporium leaf spot (*Cochiobolus miyabeanus*), powdery mildew of various host plants, such as powdery mildew of barley and wheat (*Erysiphe graminis*), oats crown rust (*Puccinia coronata*), rust of other plants, tomato late blight (*Phytophthora infestans*), late blight or Phytophthora rots of other plants, downy mildew of various plants, such as cucumber downy mildew (*Pseudoperonospora cubensis*) and grape downy mildew (*plasmopara viticola*), apple scab (*Venturia inaequalis*), apple alternaria leaf spot (*Alternaria mali*), pear black spot (*Alternaria kikuchiana*), and citrus melanose (*Diaporthe citri*).

The agricultural and horticultural fungicide of the present invention has a marked fungicidal effect on the above-exemplified diseases which damage paddy field crops, upland crops, fruit trees, vegetables, other crops, flowers and ornamental plants, and the like. Therefore, the desired effects of the agricultural and horticultural fungicide of the present invention can be obtained by applying the fungicide to the paddy field water, stalks and leaves of fruit trees, vegetables, other crops, flowers and ornamental plants, soil, etc., at a season at which the diseases are expected to occur, before their occurrence or at the time when their occurrence is confirmed.

When the N-substituted phenylcarbamic acid derivative of the general formula (I) of the present invention is used as an agricultural and horticultural fungicide, it is generally prepared into conveniently usable forms according to an ordinary manner for preparation of agrochemicals.

That is, the N-substituted phenylcarbamic acid derivative of the general formula (I) of the present invention and, optionally, an adjuvant are blended with a suitable inert carrier in a proper proportion and prepared into a suitable preparation form such as a suspension, emulsifiable concentrate, soluble concentrate, wettable powder, granules, dust or tablets through dissolution, dispersion, suspension, mixing, impregnation, adsorption or sticking.

The inert carrier used in the present invention may be either solid or liquid. As the solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, i.e. synthetic, high-dispersion silicic acid, also called finely divided hydrated silica or hydrated silicic acid, some of commercially available products contain silicate as the major component), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicon oils may also be used as a defoaming agent.

The content of the active ingredient may be varied as required. In dusts or granules, the suitable content thereof is from 0.01 to 50% by weight. In emulsifiable concentrates or flowable wettable powders, it is also from 0.01 to 50% by weight.

The agricultural and horticultural fungicide containing the N-substituted phenylcarbamic acid derivative of the general formula (I) of the present invention as an active ingredient is used to control various diseases in the following manner. That is, it is applied to a crop on which the diseases are expected to occur, or a site where the occurrence of the diseases is undesirable, as it is or after being properly diluted with or suspended in water or the like, in an amount effective for control of the diseases.

The applying dosage of the agricultural and horticultural fungicide containing the N-substituted phenylcarbamic acid derivative of the general formula (I) of the present invention as an active ingredient is varied depending upon various factors such as a purpose, diseases to be controlled, a growth state of a plant, tendency of disease occurrence, weather, environmental conditions, a preparation form, an application method, an application site and application time. It may be properly chosen in the range of 0.1 g to 1 kg (in terms of the active ingredient) per 10 ares depending upon purposes.

The agricultural and horticultural fungicide containing the N-substituted phenylcarbamic acid derivative of the general formula (I) of the present invention as an active ingredient may be used in admixture with other agricultural and horticultural fungicides in order to expand both spectrum of controllable diseases and the period of time when effective applications are possible or to reduce the dosage.

Typical preparation examples and test examples of the present invention are described below but they should not be construed as limiting the scope of the invention.

In the preparation examples, parts are all by weight.

Formulation Example 1

| Each compound of the invention | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| Each compound of the invention | 3 parts |
| Clay powder | 82 parts |
| Diatomaceous earth powder | 15 parts |

A dust was prepared by mixing uniformly and grinding the above ingredients.

Formulation Example 3

| Each compound of the invention | 5 parts |
| --- | --- |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| Each compound of the invention | 20 parts |
| --- | --- |
| Mixture of kaolin and synthetic, high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Controlling effect on barley powdery mildew

Potted barley plants at the 1 leaf stage were inoculated with spores of powdery mildew fungus (*Erysiphe graminis* f. sp. *hordei*) by sprinkling. After 24 hours, they were sprayed with a 200 ppm liquid chemical containing each compound of the present invention as active ingredient, and then allowed to stand in a room thermostated at 25° C.

After one week of the inoculation, the lesion area of each leaf was measured and then compared with that on the untreated plot, whereby the effect was judged according to the following criterion.

| Effect | Controlling degree (%) |
| --- | --- |
| A | 100–95 |
| B | 94–80 |
| C | 79–60 |
| D | 59–0 |

The results obtained are shown in Table 5.

Test Example 2

Controlling effect on apple scab

Potted apple plants at the 5 leaf stage were sprayed with a 200 ppm liquid chemical containing each compound of the present invention as active ingredient. After 24 hours, they were inoculated with a suspension of conidia of scab fungus (*Venturia inaequalis*) by spraying.

After the inoculation, the plants were placed in a moist chamber at 15° C. for 2 weeks to cause the disease sufficiently. Then, the degree of lesions of each leaf was investigated and the effect was judged according to the same criterion as described in Test Example 1.

The results obtained are shown in Table 5.

Test Example 3

Controlling effect on tomato late blight

Potted tomato plants at the 4 leaf stage were sprayed with a 200 ppm liquid chemical containing each compound of the present invention as active ingredient. After 24 hours, they were inoculated with a suspension of zoospores of late blight fungus (*Phytophthora infestans*) by spraying. The plants were placed in a moist chamber at 25° C. for 1 day and then a greenhouse for 6 days to cause the disease sufficiently. Thereafter, the degree of lesions of each leaf was investigated and then compared with that on the untreated plot, whereby the effect was judged according to the same criterion as described in Test Example 1.

The results obtained are shown in Table 5.

Test Example 4

Controlling effect (curative effect) on cucumber gray mold

The cotyledons of potted cucumber plants at the 1 leaf stage were cut off and each of them was inoculated with a mycelial tuft of gray mold fungus (*Botrytis cinerea*) cultured on PSA medium. After having been placed in a moist chamber at 15° C. for 24 hours, the cotyledons were immersed in a 200 ppm liquid chemical containing each compound of the present invention as active ingredient.

Then, the cotyledons were placed in a moist chamber at 15° C. for 3 days to cause the disease sufficiently, after which the diameter of lesions was measured and then compared with that on the untreated plot, whereby the effect was judged according to the same criterion as described in Test Example 1.

The results obtained are shown in Table 5.

Test Example

Controlling effect (preventive effect) on cucumber gray mold

Potted cucumber plants at the 1 leaf stage were sprayed with a 200 ppm liquid chemical containing each compound of the present invention as active ingredient. After 24 hours, the cotyledons of the plants were cut off and each of them was inoculated with a mycelial tuft of gray mold fungus (*Botrytis cinerea*) cultured on PSA medium.

After the inoculation, the cotyledons were placed in a moist chamber at 15° C. for 5 days to cause the disease sufficiently, after which the diameter of lesions was measured and then compared with that on the untreated plot, whereby the effect was judged according to the same criterion as described in Test Example 1.

The results obtained are shown in Table 5.

TABLE 5

| No | Erg | Vei | Phi | Boc Curing | Boc Prevention |
| --- | --- | --- | --- | --- | --- |
| 10 | A | A | B | A | A |
| 11 | A | A | B | A | A |
| 12 | A | A | A | A | A |
| 15 | A | A | A | A | A |
| 16 | A | A | A | A | A |
| 17 | A | A | B | A | A |
| 21 | A | A | B | A | A |
| 22 | A | A | B | A | A |
| 27 | A | A | B | C | A |
| 32 | A | A | B | A | B |
| 33 | A | A | A | A | A |
| 35 | A | A | C | A | A |
| 37 | A | A | A | C | A |
| 38 | A | A | B | A | A |
| 39 | A | A | B | A | A |
| 40 | A | A | A | A | A |
| 41 | A | A | C | A | C |
| 42 | A | A | B | B | A |
| 43 | A | B | B | A | A |
| 44 | A | A | B | A | A |
| 45 | A | — | B | A | B |
| 49 | A | A | C | A | — |
| 50 | A | A | C | A | C |
| 51 | A | A | — | A | — |
| 54 | A | A | — | — | C |
| 55 | A | A | — | A | — |
| 56 | A | — | A | — | A |
| 58 | A | — | B | A | A |
| 61 | A | — | B | A | A |
| 62 | A | — | C | — | B |
| 64 | A | — | A | — | A |
| 67 | A | — | A | A | A |
| 68 | A | — | C | B | C |
| 69 | A | A | — | B | — |

TABLE 5-continued

| No | Erg | Vei | Phi | Boc Curing | Boc Prevention |
|---|---|---|---|---|---|
| 70 | A | A | B | A | B |
| 71 | A | — | B | A | A |
| 75 | B | — | B | A | C |
| 78 | A | — | — | A | C |
| 82 | A | B | — | A | C |
| 84 | C | A | — | A | B |
| 85 | A | A | A | A | D |
| 86 | A | A | A | B | B |
| 87 | A | A | — | A | B |
| 88 | — | A | B | A | A |
| 89 | — | A | C | A | B |
| 90 | A | — | — | A | — |
| 92 | A | A | A | A | B |
| 93 | A | — | B | — | A |
| 94 | A | A | B | — | A |
| 100 | A | A | B | A | A |
| 101 | A | A | B | A | C |
| 102 | A | A | B | A | B |
| 106 | A | — | A | A | A |
| 111 | — | — | — | B | — |
| 113 | A | A | A | A | — |
| 117 | A | — | — | — | — |
| 152 | A | — | A | A | A |
| 153 | A | — | — | A | B |
| 154 | A | — | A | C | — |
| 155 | A | — | B | A | A |
| 158 | A | — | A | A | C |
| 159 | A | — | B | A | A |
| 166 | A | — | — | A | A |
| 171 | A | — | — | B | C |
| 173 | A | A | — | — | — |
| 176 | A | — | — | — | — |
| 183 | A | — | — | A | B |
| 185 | A | A | — | B | C |
| 188 | B | A | — | — | — |
| 197 | A | A | C | A | B |
| 200 | A | A | — | — | — |
| 201 | A | A | C | — | — |
| 203 | A | B | — | — | A |

NOTE:
Erg barley powdery mildew
Vei apple scab
Phi tomato late blight
Boc cucumber gray mold

What is claimed is:

1. A compound represented by the formula:

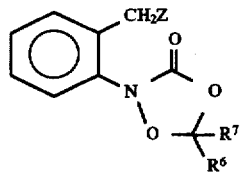

wherein Z is a halogen atom or

wherein $R^6$ and $R^7$, which may be the same or different, are hydrogen atoms, $(C_{1-6})$alkyl groups, $(C_{3-6})$ cycloalkyl groups, unsubstituted phenyl groups, or substituted phenyl groups having 1 to 5 substituents which may be the same or different and are selected from the group consisting of halogen atoms, cyano group, nitro group and $(C_{1-6})$alklyl groups, $R^6$ and $R^7$ being able to be taken together to represent a $(C_{2-6})$alkylene group, $R^3$ is a $(C_{1-6})$alkyl group or a halo$(C_{1-6})$alkyl group and $R^4$ and $R^5$, which may be the same or different, are hydrogen atoms; cyano groups; $(C_{1-6})$alkyl groups; halo$(C_{1-6})$alkyl groups; $(C_{3-6})$cycloalkyl groups; halo $(C_{3-6})$cycloalkyl groups; $(C_{3-6})$ cycloalkyl$(C_{1-6})$alkyl groups; $(C_{1-6})$alkoxy groups; halo$(C_{1-6})$ alkoxy groups; $(C_{1-6})$alkylthio groups; halo$(C_{1-6})$alkylthio groups; $(C_{1-6})$alkoxy$(C_{1-6})$alkyl groups; $(C_{1-6})$alkylthio$(C_{1-6})$ alkyl groups; $(C_{2-6})$alkenyl groups; halo$(C_{2-6})$alkenyl groups; $(C_{3-6})$cycloalkenyl groups; $(C_{2-6})$alkynyl groups; halo$(C_{2-6})$alkynyl groups; $(C_{1-6})$alkylcarbonyl groups; $(C_{1-6})$alkoxycarbonyl groups; unsubstituted phenyl groups; substituted phenyl groups having 1 to 5 substituents which may be the same or different and are selected from the group consisting of halogen atoms, cyano group, nitro group, formyl group, $(C_{1-6})$ alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{2-6})$alkenyloxy groups, halo$(C_{2-6})$alkenyloxy groups, $(C_{2-6})$alkynyloxy groups, halo$(C_{2-6})$alkynyloxy groups, $(C_{1-6})$ alkylcarbonyl groups, $(C_{1-6})$alkoxycarbonyl groups, di$(C_{1-6})$alkylamino groups, di$(C_{2-6})$alkenylamino groups, di$(C_{2-6})$alkynylamino groups, unsubstituted phenyl$(C_{1-6})$alkyl groups, substituted phenyl$(C_{1-6})$ alkyl groups having 1 to 5 substituents which may be the same or different and are selected from the group consisting of $(C_{1-6})$alkyl groups, $(C_{1-6})$alkoxy groups and cyano group, unsubstituted phenoxy group, substituted phenoxy groups having 1 to 5 substituents which may be the same or different and are selected from the group consisting of $(C_{1-6})$alkyl groups, $(C_{1-6})$alkoxy groups and cyano group, unsubstituted heteroaryloxy groups, substituted heteroaryloxy groups having 1 to 5 substituents which may be the same or different and are selected from the group consisting of $(C_{1-6})$alkyl groups, $(C_{1-6})$alkoxy groups and cyano group, unsubstituted benzyloxy group, substituted benzyloxy groups having on the ring 1 to 5 substituents which may be the same or different and are selected from the group consisting of $(C_{1-6})$alkyl groups, $(C_{1-6})$alkoxy groups and cyano group, $(C_{1-6})$-alkoxyimino$(C_{1-6})$alkyl groups, $(C_{1-6})$alkylenedioxy groups, and $(C_{2-6})$alkylene groups; unsubstituted phenoxy groups; substituted phenoxy groups having 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$ alkoxy groups, halo$(C_{1-6})$alkoxy groups, $(C_{1-6})$ alkylthio groups, halo$(C_{1-6})$alkylthio groups, $(C_{1-6})$ alkoxyimino$(C_{1-6})$alkyl groups and $(C_{1-3})$ alkylenedioxy groups; unsubstituted phenylthio groups; substituted phenylthio groups having 1 to 5 substituents which may be the same or different and are selected from the group consisting of halogen atoms, cyano group, nitro group, $(C_{1-6})$alkyl groups, halo $(C_{1-6})$ alkyl groups, $(C_{1-6})$alkoxy groups, halo$(C_{1-6})$ alkoxy groups, $(C_{1-6})$alkylthio groups, halo$(C_{1-6})$ alkylthio groups, $(C_{1-6})$alkoxyimino$(C_{1-6})$alkyl groups and $(C_{1-3})$alkylenedioxy groups; unsubstituted phenyl $(C_{1-6})$alkyl groups; substituted phenyl $(C_{1-6})$alkyl groups having on the ring 1 to 5 substituents which may be the same or different and are selected from the group consisting of halogen atoms, cyano group, nitro group, $(C_{1-6})$alkyl groups, halo$(C_{1-6})$alkyl groups, $(C_{1-6})$ alkoxy groups, halo$(C_{1-6})$allkoxy groups, $(C_{1-6})$ alkylthio groups, halo$(C_{1-6})$alkylthio groups, $(C_{1-6})$ alkoxyimino$(C_{1-6})$alkyl groups and $(C_{1-3})$ alkylenedioxy groups; unsubstituted phenyl$(C_{2-6})$ alkenyl groups; substituted phenyl($C_{2-6}$)alkenyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenylcarbonyl groups; substituted phenylcarbonyl groups having 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$)alkoxy groups, halo ($C_{1-6}$)alkoxy groups, ($C_{1-6}$)alkylthio groups, halo ($C_{1-6}$)alkylthio groups, ($C_{1-6}$)alkoxyimino($C_{1-6}$)alkyl groups and ($C_{1-3}$)alkylenedioxy groups; unsubstituted phenoxycarbonyl groups; substituted phenoxycarbonyl groups having 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenoxy ($C_{1-6}$) alkyl groups; substituted phenoxy($C_{1-6}$)alkyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenylthio ($C_{1-6}$) alkyl groups; substituted phenylthio($C_{1-6}$)alkyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenyl($C_{1-6}$) alkylthio groups; substituted phenyl ($C_{1-6}$)alkylthio groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenyl ($C_{1-6}$) alkylcarbonyl groups; substituted phenyl($C_{1-6}$) alkylcarbonyl groups having on the ring 1 to 5 substituents which may be the same or different and are selected from the group consisting of halogen atoms, cyano group, nitro group, ($C_{1-6}$)alkyl groups, halo ($C_{1-6}$)alkyl groups, ($C_{1-6}$)alkoxy groups, halo($C_{1-6}$) alkoxy groups, ($C_{1-6}$)alkylthio groups, halo($C_{1-6}$) alkylthio groups, ($C_{1-6}$)alkoxyimino($C_{1-6}$)alkyl groups and ($C_{1-3}$)alkylenedioxy groups; unsubstituted phenyl ($C_{1-6}$)alkoxycarbonyl groups; substituted phenyl($C_{1-6}$) alkoxycarbonyl groups having on the ring 1 to 5 substituents which may be the same or different and are selected from the group consisting of halogen atoms, cyano group, nitro group, ($C_{1-6}$)alkyl groups, halo ($C_{1-6}$)alkyl groups, ($C_{1-6}$)alkoxy groups, halo($C_{1-6}$) alkoxy groups, ($C_{1-6}$)alkylthio groups, halo($C_{1-6}$) alkylthio groups, ($C_{1-6}$)alkoxyimino($C_{1-6}$)alkyl groups and ($C_{1-3}$)alkylenedioxy groups; 5-to 7-membered heterocyclic rings having 1 to 3 heteroatoms which may be the same or different and are selected from the group consisting of oxygen atom, sulfur atom and nitrogen atom; heterocyclic rings having a benzene ring condensed therewith; or heterocyclic rings having a ($C_{1-3}$)cycloalkane group condensed therewith; the above heterocyclic rings being able to have one or more substituents which may be the same or different and are selected from the group consisting of halogen atoms, cyano group, nitro group, ($C_{1-6}$)alkyl groups, halo ($C_{1-6}$)alkyl groups, ($C_{1-6}$)alkoxy groups, halo($C_{1-6}$) alkoxy groups, ($C_{1-6}$)alkylthio groups, halo($C_{1-6}$) alkylthio groups, ($C_{1-6}$)alkoxycarbonyl groups, unsubstituted phenyl group, substituted phenyl groups having 1 to 5 substituents which may be the same or different and are selected from the group consisting of halogen atoms and ($C_{1-6}$)alkyl groups, phenyl($C_{1-6}$)alkyl groups, pyridyl group, pyrimidyl group and dioxolane group, and Y is an oxygen atom or a sulfur atom.

2. A compound represented by the general formula (V):

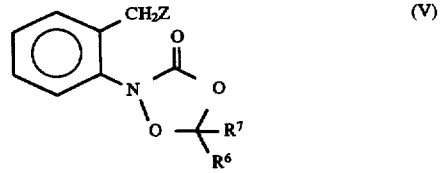

wherein $R^6$ and $R^7$, which may be the same or different, are hydrogen atoms, ($C_{1-6}$)alkyl groups, ($C_{3-6}$)cycloalkyl groups, unsubstituted phenyl groups, or substituted phenyl groups having 1 to 5 substituents which may be the same or different and are selected from the group consisting of halogen atoms, cyano group, nitro group and ($C_{1-6}$)alklyl groups. $R^6$ and $R^7$ being able to be taken together to represent a ($C_{2-6}$)alkylene group, and Z is a halogen atom.

3. A compound represented by the general formula (VI):

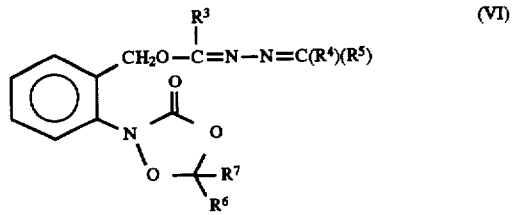

wherein $R^6$ and $R^7$, which may be the same or different are hydrogen atoms, ($C_{1-6}$)alkyl groups, ($C_{3-6}$) cycloalkyl groups, unsubstituted phenyl groups, or substituted phenyl groups having 1 to 5 substituents which may be the same or different and are selected from the group consisting of halogen atoms, cyano group, nitro group and ($C_{1-6}$)alklyl groups, $R^6$ and $R^7$ being able to be taken together to represent a ($C_{2-6}$)alkylene group, $R^3$ is a ($C_{1-6}$)alkyl group or a halo($C_{1-6}$)alkyl group and $R^4$ and $R^5$, which may be the same or different, are hydrogen atoms; cyano groups; ($C_{1-6}$)alkyl groups; halo($C_{1-6}$)alkyl groups; ($C_{3-6}$)cycloalkyl groups; halo ($C_{3-6}$)cycloalkyl groups; ($C_{3-6}$) cycloalkyl($C_{1-6}$)alkyl groups; ($C_{1-6}$)alkoxy groups; halo($C_{1-6}$) alkoxy groups; ($C_{1-6}$)alkylthio groups; halo($C_{1-6}$)alkylthio groups;

($C_{1-6}$)alkoxy($C_{1-6}$)alkyl groups; ($C_{1-6}$)alkylthio($C_{1-6}$) alkyl groups; ($C_{2-6}$)alkenyl groups; halo($C_{2-6}$)alkenyl groups; ($C_{3-6}$) cycloalkenyl groups; ($C_{2-6}$)alkynyl groups; halo($C_{2-6}$)alkynyl groups; ($C_{1-6}$)alkylcarbonyl groups; ($C_{1-6}$)alkoxycarbonyl groups; unsubstituted phenyl groups; substituted phenyl groups having 1 to 5 substituents which may be the same or different and are selected from the group consisting of halogen atoms, cyano group, nitro group, formyl group, ($C_{1-6}$)alkyl groups, halo($C_{1-6}$)alkyl groups, ($C_{1-6}$)alkoxy groups halo($C_{1-6}$)alkoxy groups, ($C_{1-6}$)alkylthio groups, halo ($C_{1-6}$)alkylthio groups, ($C_{2-6}$)alkenyloxy groups, halo ($C_{2-6}$)alkenyloxy groups, ($C_{2-6}$)alkynyloxy groups, halo($C_{2-6}$)alkynyloxy groups, ($C_{1-6}$)alkylcarbonyl groups, ($C_{1-6}$)alkoxycarbonyl groups, di($C_{1-6}$) alkylamino groups, di($C_{2-6}$)alkenylamino groups, di($C_{2-6}$)alkynylamino groups, unsubstituted phenyl ($C_{1-6}$)alkyl groups, substituted phenyl($C_{1-6}$)alkyl groups having 1 to 5 substituents which may be the same or different and are selected from the group consisting of ($C_{1-6}$)alkyl groups, ($C_{1-6}$)alkoxy groups and cyano group, unsubstituted phenoxy group, substituted phenoxy groups having 1 to 5 substituents which may be the same or different and are selected from the group consisting of ($C_{1-6}$)alkyl groups, ($C_{1-6}$)alkoxy groups and cyano group, unsubstituted heteroaryloxy groups, substituted heteroaryloxy groups having 1 to 5 substituents which may be the same or different and are selected from the group consisting of ($C_{1-6}$)alkyl groups, ($C_{1-6}$)alkoxy groups and cyano group, unsubstituted benzyloxy group, substituted benzyloxy groups having on the ring 1 to 5 substituents which may be the same or different and are selected from the group consisting of, ($C_{1-6}$)alkyl groups, ($C_{1-6}$)alkoxy groups and cyano group, ($C_{1-6}$)-alkoxyimino($C_{1-6}$)alkyl groups, ($C_{1-3}$)alkylenedioxy groups, and ($C_{2-6}$)alkylene groups; unsubstituted phenoxy groups; substituted phenoxy groups having 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenylthio groups; substituted phenylthio groups having 1 to 5 substituents which may be the same or different and are selected from the group consistiting of halogen atoms, cyano group, nitro group, ($C_{1-6}$)alkyl groups, halo ($C_{1-6}$)alkyl groups, ($C_{1-6}$)alkoxy groups, halo($C_{1-6}$) alkoxy groups, ($C_{1-6}$)alkylthio groups, halo($C_{1-6}$) alkylthio groups, ($C_{1-6}$)alkoxyimino($C_{1-6}$)alkyl groups and ($C_{1-3}$)alkylenedioxy groups; unsubstituted phenyl ($C_{1-6}$)alkyl groups; substituted phenyl($C_{1-6}$)alkyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenyl($C_{2-6}$) alkenyl groups; substituted phenyl ($C_{2-6}$)alkenyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and halo($C_{1-3}$) alkylenedioxy groups; unsubstituted phenylcarbonyl groups; substituted phenylcarbonyl groups having 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$)alkoxy groups, halo ($C_{1-6}$)alkoxy groups,($C_{1-6}$)alkylthio groups, halo($C_{1-6}$) alkylthio groups, ($C_{1-6}$)alkoxyimino($C_{1-6}$)alkyl groups and ($C_{1-3}$)alkylenedioxy groups; unsubstituted phenoxycarbonyl groups; substituted phenoxycarbonyl groups having 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups halo($C_{1-6}$)alkoxy groups, ($C_{1-6}$)alkylthio groups, halo($C_{1-6}$)alkylthio groups, ($C_{1-6}$)alkoxyimino ($C_{1-6}$)alkyl groups and ($C_{1-3}$)alkylenedioxy groups; unsubstituted phenoxy ($C_{1-6}$)alkyl groups; substituted phenoxy($C_{1-6}$)alkyl groups having on the ring 1 to 5 substituents which may be the same or different and are selected from the group consisting of halogen atoms, cyano group, nitro group, ($C_{1-6}$)alkyl groups, halo ($C_{1-6}$)alkyl groups, ($C_{1-6}$)alkoxy groups, halo($C_{1-6}$) alkoxy groups, ($C_{1-6}$)alkylthio groups, halo($C_{1-6}$) alkylthio groups, ($C_{1-6}$)alkoxyimino($C_{1-6}$)alkyl groups and ($C_{1-3}$)alkylenedioxy groups; unsubstituted phenylthio ($C_{1-6}$)alkyl groups; substituted phenylthio ($C_{1-6}$)alkyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$)alkoxy groups, halo($C_{1-6}$)alkoxy groups, ($C_{1-6}$)alkylthio groups, halo($C_{1-6}$)alkylthio groups, ($C_{1-6}$)alkoxyimino($C_{1-6}$)alkyl groups and ($C_{1-3}$) alkylenedioxy groups; unsubstituted phenyl($C_{1-6}$) alkylthio groups; substituted phenyl($C_{1-6}$)alkylthio groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxylthio($C_{1-6}$)alkyl groups and ($C_{1-3}$)alkylenedioxy groups; unsubstituted phenyl ($C_{1-6}$)alkylcarbonyl groups; substituted phenyl($C_{1-6}$)alkylcarbonyl groups having on the ring 1 to 5 substituents which may be the same or different and are selected from the group consisting of halogen atoms, cyano group, nitro group, ($C_{1-6}$)alkyl groups, halo($C_{1-6}$)alkyl groups, ($C_{1-6}$) alkoxy groups, halo($C_{1-6}$)alkoxy groups, ($C_{1-6}$) alkylthio groups, halo($C_{1-6}$)alkylthio groups, ($C_{1-6}$) alkoxyimino($C_{1-6}$)alkyl groups and ($C_{1-3}$) alkylenedioxy groups; unsubstituted phenyl($C_{1-6}$) alkoxycarbonyl groups; substituted phenyl($C_{1-6}$) alkoxycarbonyl groups having on the ring 1 to 5 substituents which may be the same or different and are selected from the group consisting of halogen atoms, cyano group, nitro group, ($C_{1-6}$)alkyl groups, halo ($C_{1-6}$)alkyl groups, ($C_{1-6}$)alkoxy groups, halo($C_{1-6}$) alkoxy groups, ($C_{1-6}$)alkylthio groups, halo($C_{1-6}$) alkylthio groups, ($C_{1-6}$)alkoxyimino($C_{1-6}$)alkyl groups and ($C_{1-3}$)alkylenedioxy groups; 5- to 7-membered heterocyclic rings having 1 to 3 heteroatoms which may be the same or different and are selected from the group consisting of oxygen atom, sulfur atom and nitrogen atom; heterocyclic rings having a benzene ring condensed therewith; or heterocyclic rings having a $(C_{3-6})$cycloalkane group condensed therewith; the above heterocyclic rings being able to have one or more substituents which may be the same or different and are selected from the group consisting of halogen atoms, cyano group, nitro group, $(C_{1-6})$alkyl groups, halo$(C_{1-6})$alkyl groups, $(C_{1-6})$alkoxy groups, halo$(C_{1-6})$alkoxy groups, $(C_{1-6})$alkylthio groups, halo$(C_{1-6})$alkylthio groups, $(C_{1-6})$alkoxycarbonyl groups, unsubstituted phenyl group, substituted phenyl groups having 1 to 5 substituents which may be the same or different and are selected from the group consisting of halogen atoms and $(C_{1-6})$alkyl groups, phenyl$(C_{1-6})$alkyl groups, pyridyl group, pyrimidyl group and dioxolane group, and Y is an oxygen atom or a sulfur atom.

\* \* \* \* \*